(12) United States Patent
Meyer et al.

(10) Patent No.: US 11,744,451 B2
(45) Date of Patent: *Sep. 5, 2023

(54) SYSTEMS FOR TRACKING PROGRESS OF AN ORTHODONTIC PROCEDURE

(71) Applicant: Align Technology, Inc., San Jose, CA (US)

(72) Inventors: Eric P. Meyer, Pleasanton, CA (US); Roman A. Roschin, Moscow (RU); Tzishing Jesse Lim, Mountain View, CA (US); Palak Mittal, Sunnyvale, CA (US); Stephan Albert Alexandre Dumothier, Houston, TX (US); Norman C. Su, San Jose, CA (US); Huameng Ivan Chu, San Mateo, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/059,387

(22) Filed: Nov. 28, 2022

(65) Prior Publication Data
US 2023/0092804 A1    Mar. 23, 2023

Related U.S. Application Data

(63) Continuation of application No. 17/882,521, filed on Aug. 5, 2022, now Pat. No. 11,589,743, which is a
(Continued)

(51) Int. Cl.
*A61C 9/00* (2006.01)
*A61B 1/24* (2006.01)
(Continued)

(52) U.S. Cl.
CPC ............ *A61B 1/24* (2013.01); *A61B 1/00009* (2013.01); *A61C 5/90* (2017.02); *A61C 9/0093* (2013.01);
(Continued)

(58) Field of Classification Search
CPC ......... A61B 1/00009; A61B 1/24; A61C 5/90; A61C 9/0053; A61C 9/0093; A61C 13/34; A61C 19/04; G06T 7/60; G06T 7/62; G06T 7/70; G06T 7/74; G06T 2207/10016; G06T 2207/30036; G06T 2207/30204; H04B 1/3877
(Continued)

(56) References Cited

U.S. PATENT DOCUMENTS 5,882,192 A * 3/1999 Bergersen ................ A61C 7/00
  433/214
6,988,893 B2 * 1/2006 Haywood ................ A61C 5/90
  600/242

(Continued)

FOREIGN PATENT DOCUMENTS

EP    1252859 A2 * 10/2002    ......... A61B 1/00041

*Primary Examiner* — Matthew M Nelson
(74) *Attorney, Agent, or Firm* — Shay Glenn LLP

(57) ABSTRACT

The present disclosure provides methods, computing device readable medium, devices, and systems that utilize a cheek retractor and/or a mobile device holder for case assessment and/or dental treatments.

28 Claims, 13 Drawing Sheets

Related U.S. Application Data continuation of application No. 17/013,511, filed on Sep. 4, 2020, which is a continuation of application No. 15/895,754, filed on Feb. 13, 2018, now Pat. No. 10,779,718.

(60) Provisional application No. 62/458,477, filed on Feb. 13, 2017.

(51) Int. Cl.
| | | |
|---|---|---|
| *A61C 19/04* | (2006.01) | |
| *A61C 13/34* | (2006.01) | |
| *G06T 7/70* | (2017.01) | |
| *A61C 5/90* | (2017.01) | |
| *H04B 1/3877* | (2015.01) | |
| *G06T 7/60* | (2017.01) | |
| *A61B 1/00* | (2006.01) | |
| *G06T 7/62* | (2017.01) | |
| *G06T 7/73* | (2017.01) | |

(52) U.S. Cl.
CPC .............. *A61C 13/34* (2013.01); *A61C 19/04* (2013.01); *G06T 7/60* (2013.01); *G06T 7/62* (2017.01); *G06T 7/70* (2017.01); *G06T 7/74* (2017.01); *H04B 1/3877* (2013.01); *A61C 9/0053* (2013.01); *G06T 2207/10016* (2013.01); *G06T 2207/30036* (2013.01); *G06T 2207/30204* (2013.01)

(58) Field of Classification Search
USPC .......................................................... 433/29
See application file for complete search history.

(56) References Cited

U.S. PATENT DOCUMENTS

| | | | |
|---|---|---|---|
| 2001/0010538 A1* | 8/2001 | Ooshima | A61B 1/0625 348/66 |
| 2004/0089962 A1* | 5/2004 | Valery | A61C 13/0004 264/16 |
| 2005/0100333 A1* | 5/2005 | Kerschbaumer | A61B 1/0676 396/16 |
| 2005/0196039 A1* | 9/2005 | Bengel | G06T 7/90 382/162 |
| 2007/0141528 A1* | 6/2007 | Kobayashi | A61B 1/24 433/29 |
| 2008/0145812 A1* | 6/2008 | Taub | A61C 9/0053 433/75 |
| 2009/0167848 A1* | 7/2009 | Eren | A61B 1/24 348/66 |
| 2010/0217130 A1* | 8/2010 | Weinlaender | A61B 1/247 600/476 |
| 2012/0205828 A1* | 8/2012 | Laubersheimer | A61C 13/0004 264/20 |
| 2014/0342301 A1* | 11/2014 | Fleer | A61B 6/14 433/102 |
| 2015/0238073 A1* | 8/2015 | Charles | A61B 1/00149 600/102 |
| 2017/0014024 A1* | 1/2017 | Wachs | A61B 1/24 |
| 2017/0027432 A1* | 2/2017 | Wachs | A61B 1/24 |
| 2017/0281313 A1* | 10/2017 | Kim | A61C 7/002 |
| 2018/0204332 A1* | 7/2018 | Salah | G06T 7/33 |
| 2018/0228359 A1* | 8/2018 | Meyer | A61C 13/34 |

* cited by examiner

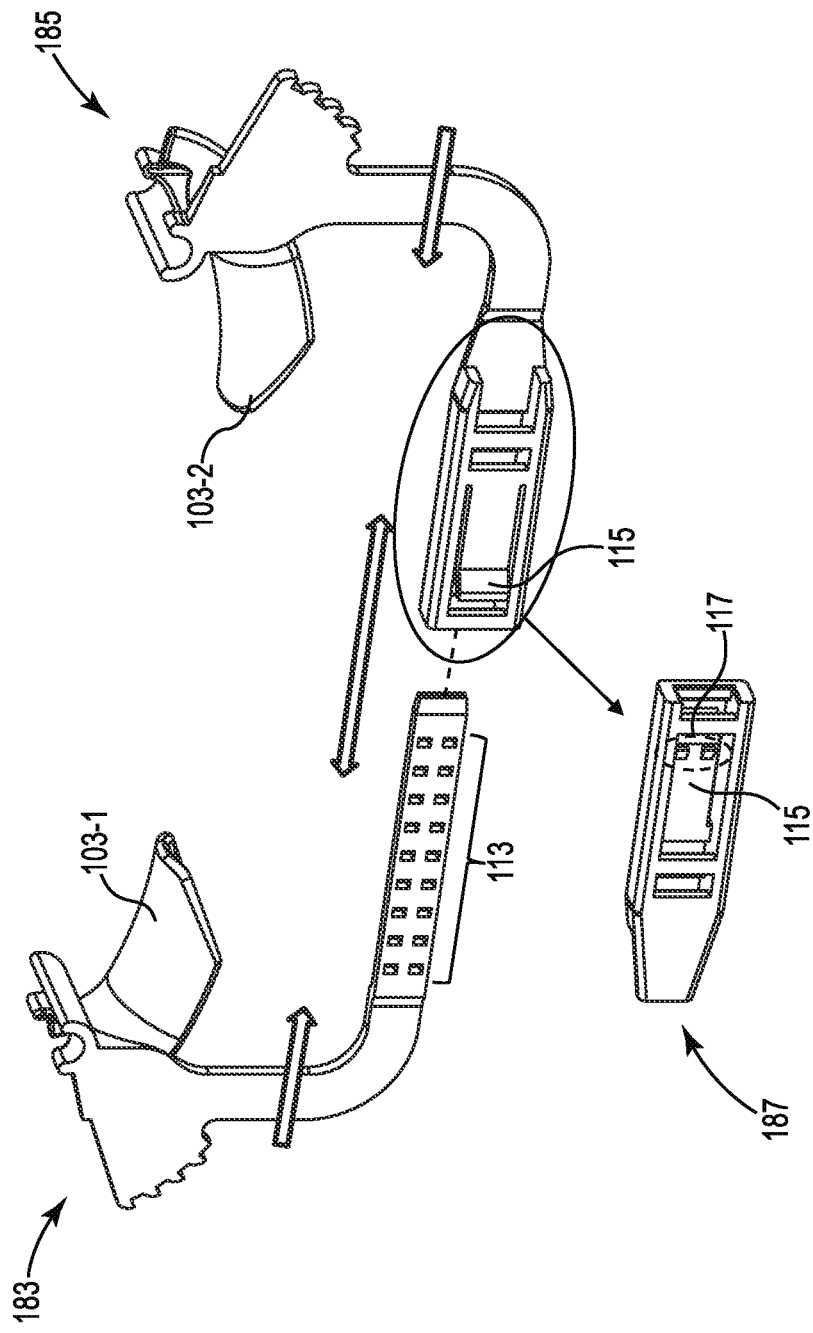

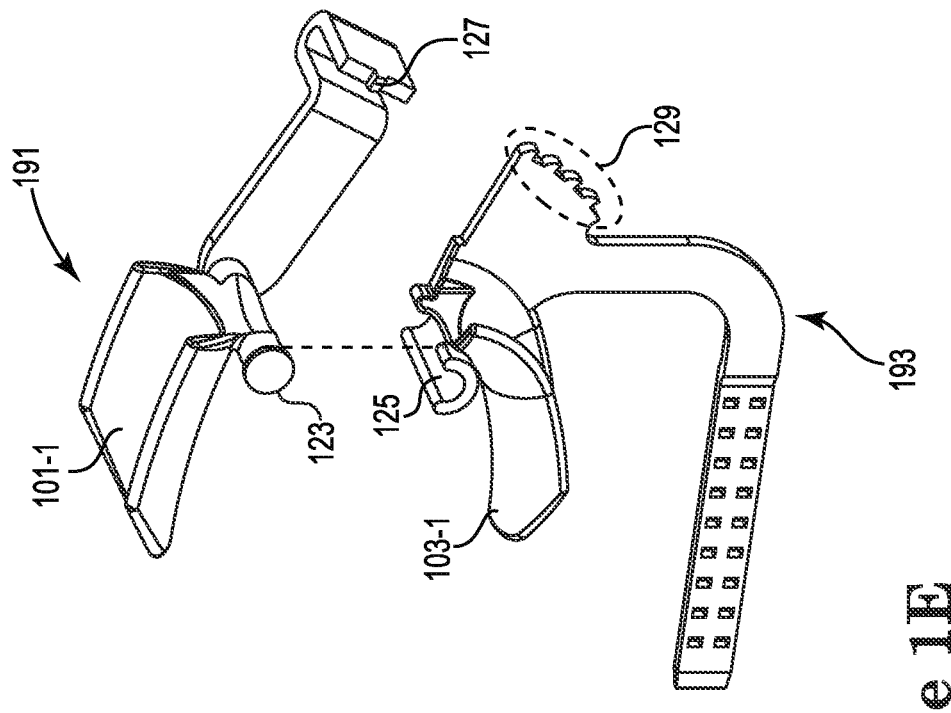
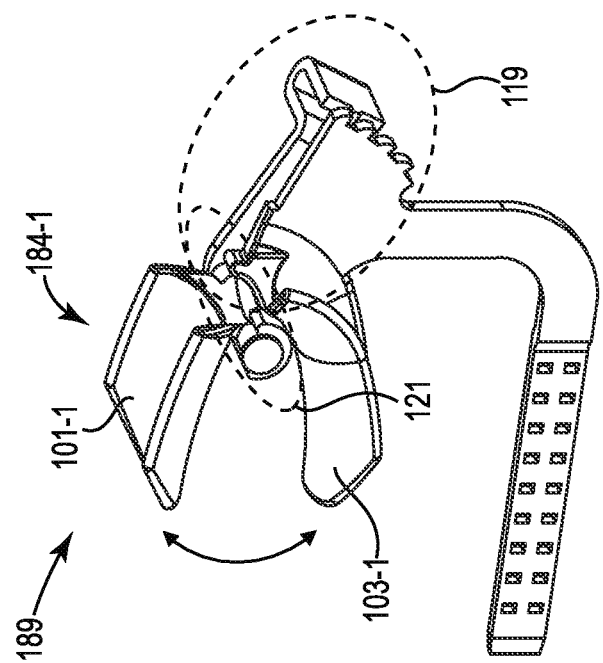
Figure 1E

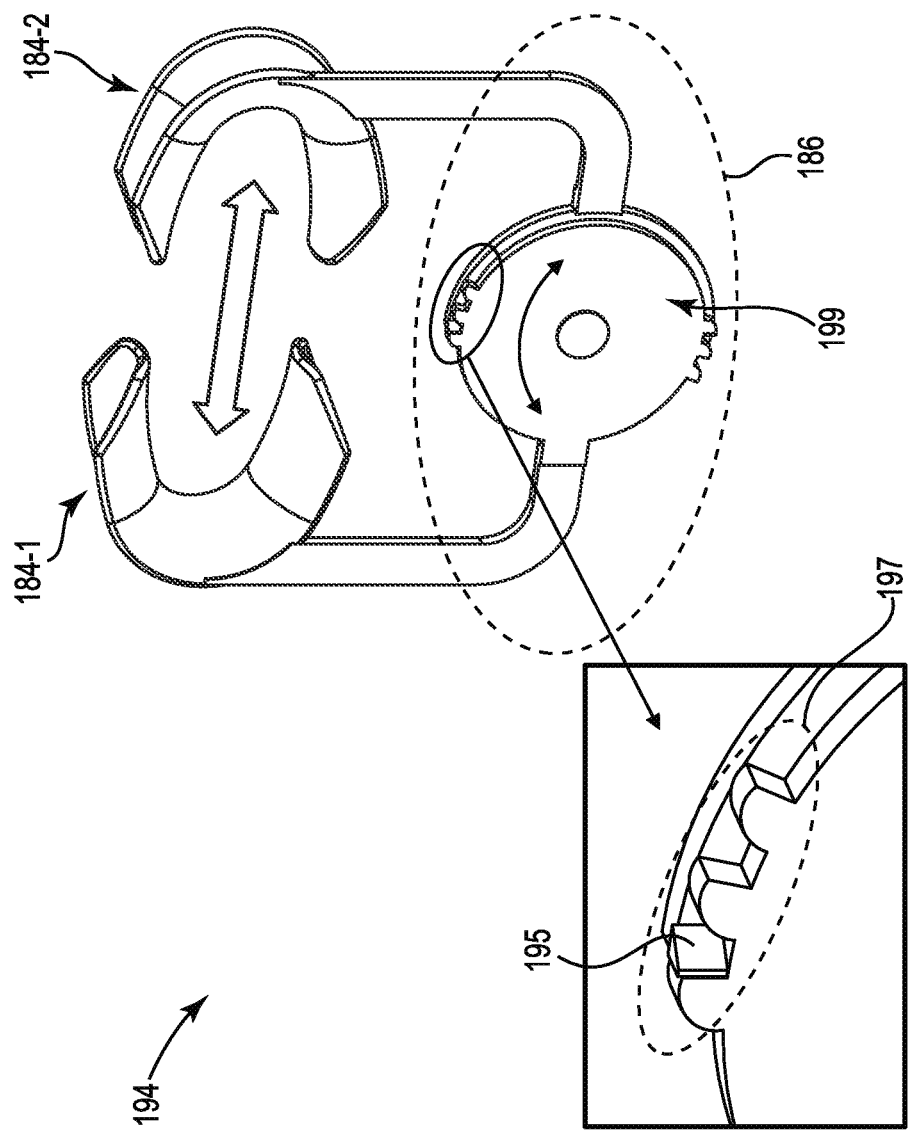

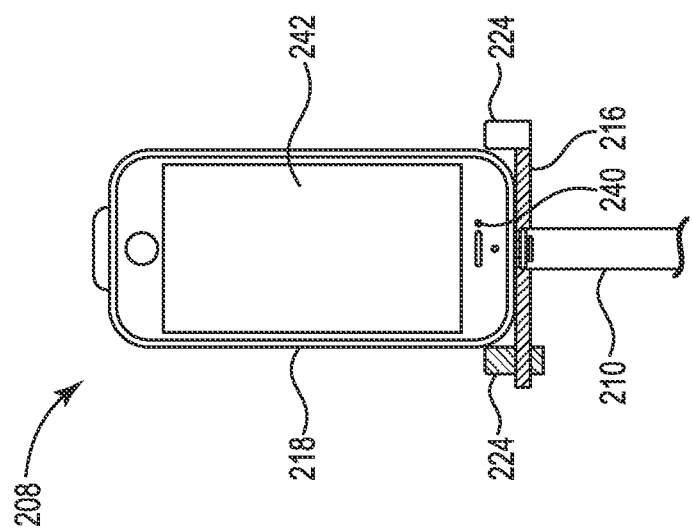
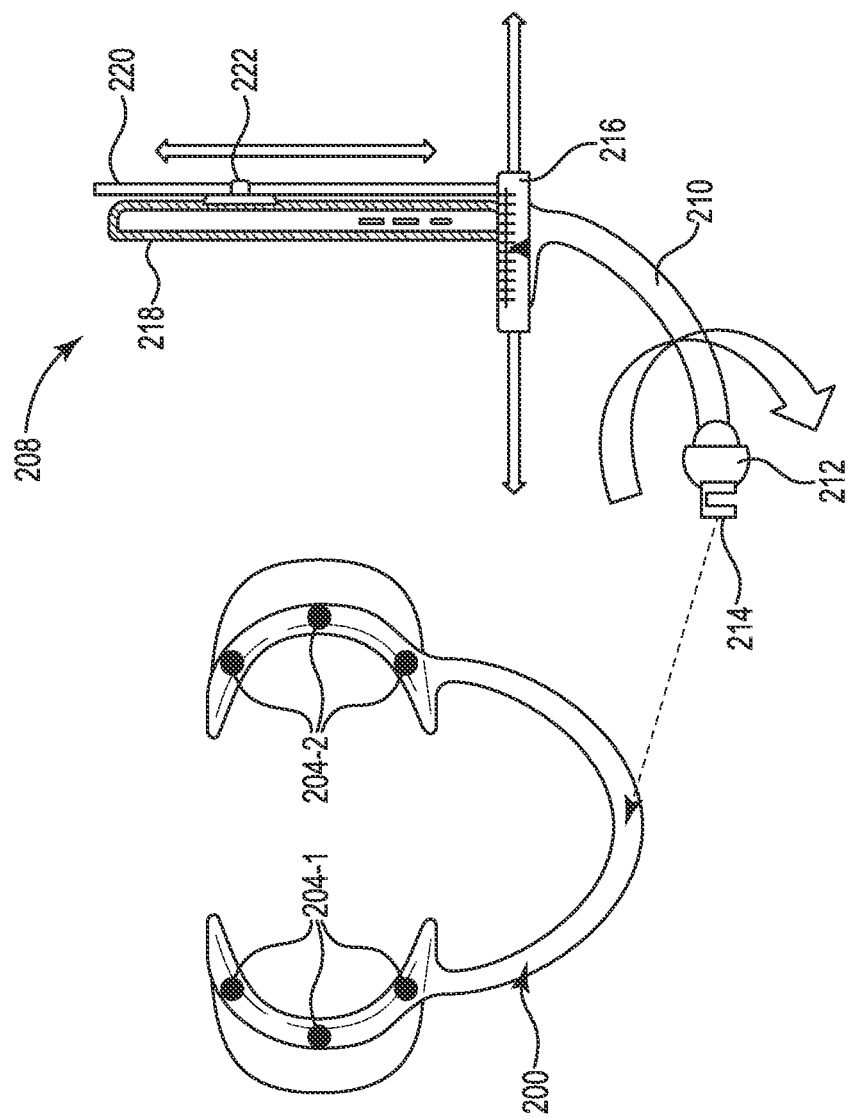
Figure 2B
Figure 2A

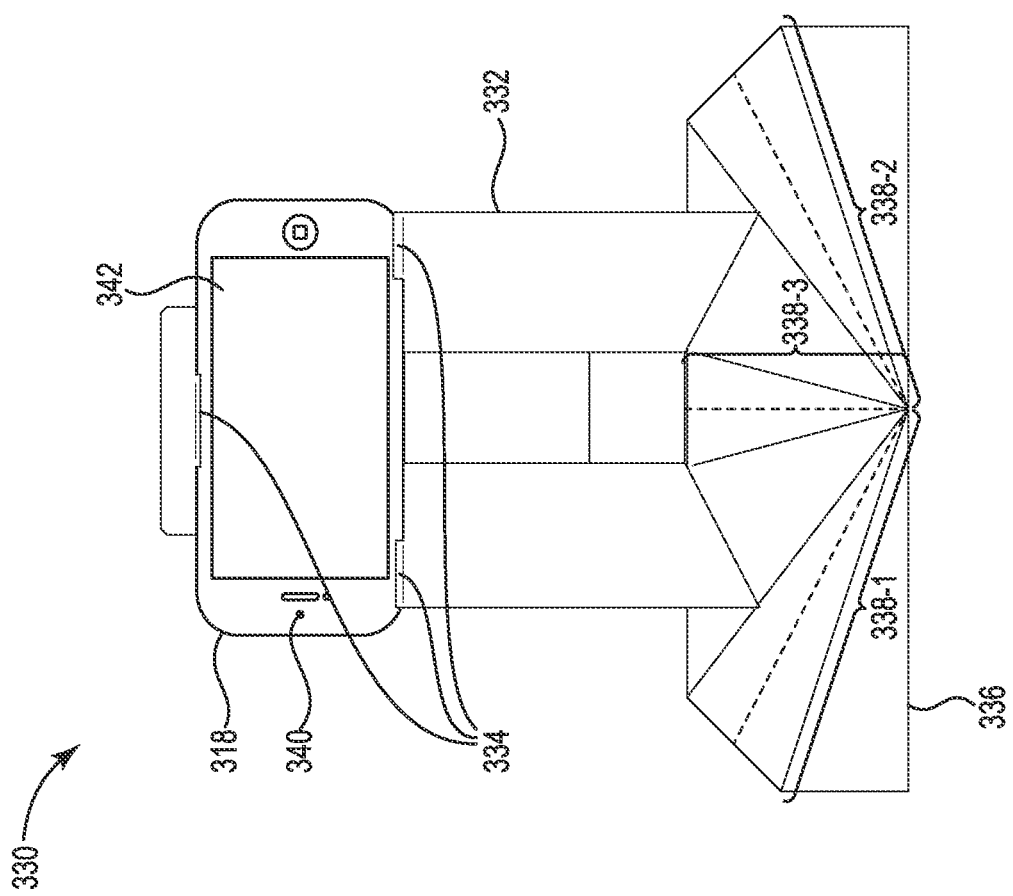

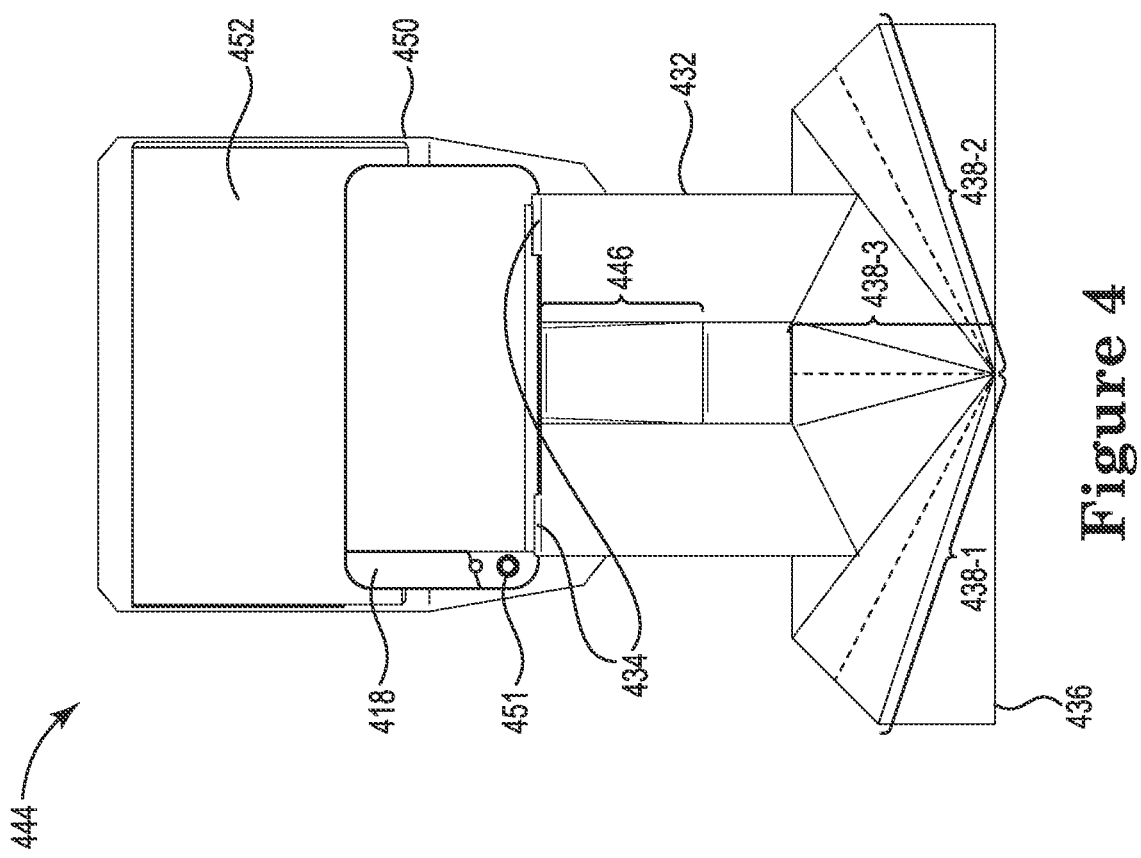

SYSTEMS FOR TRACKING PROGRESS OF AN ORTHODONTIC PROCEDURE

CLAIM OF PRIORITY

This application is a continuation of U.S. patent application Ser. No. 17/882,521, filed Aug. 5, 2022, titled "CHEEK RETRACTOR AND MOBILE DEVICE HOLDER," now U.S. Patent Application Publication No. 2022/0369915, which is a continuation of U.S. patent application Ser. No. 17/013,511, filed Sep. 4, 2020, titled "CHEEK RETRACTOR AND MOBILE DEVICE HOLDER," now U.S. Patent Application Publication No. 2020/0397273, which is a continuation of U.S. patent application Ser. No. 15/895,754, filed Feb. 13, 2018, titled "CHEEK RETRACTOR AND MOBILE DEVICE HOLDER," now U.S. Pat. No. 10,779,718, which claims the benefit of U.S. Provisional Patent Application No. 62/458,477, filed Feb. 13, 2017, and titled "CHEEK RETRACTOR AND MOBILE DEVICE HOLDER," each of which is herein incorporated by reference in its entirety.

BACKGROUND

The present disclosure provides devices, computing device readable medium, and systems that utilize a cheek retractor and/or a mobile device holder for case assessment and/or dental treatments. Dental treatments involve restorative and/or orthodontic procedures to improve the quality of life of a patient.

For example, restorative procedures may be designed to implant a dental prosthesis (e.g., a crown, bridge, inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth or a jaw of a patient over a period of time.

As an example, orthodontic repositioning may be provided through a dental process that uses positioning appliances for realigning teeth. Such appliances may utilize a shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement. Appliances can also be used for other dental conditions, such as application of medications, appliances to help with sleep apnea, and other issues.

Such systems typically utilize a set of appliances that can be used serially such that, as the teeth move, a new appliance from the set can be implemented to further move the teeth without having to take a new impression of the patient's teeth at every increment of tooth movement in order to make each successive appliance. The same attachments may be utilized or attachments may be added, removed, or replaced with other attachment shapes that may impart different force characteristics than a previous appliance and attachment combination (i.e., appliance and one or more attachments).

Dental treatments with a set of appliances may involve repeated patient visits to an orthodontist in order to verify the dental treatment is proceeding as anticipated. For instance, an orthodontist may determine during a patient visit that the orthodontic procedure, such as repositioning misaligned teeth, is not proceeding as planned and may alter the procedure. Further, a prospective patient may visit an orthodontist to determine whether a dental treatment can work for the particular patient.

Visits to a treatment professional, such as an orthodontist, can be time consuming. A patient and/or a prospective patient may need to significantly alter their daily schedule in order to visit an orthodontist. Therefore, using a camera to take images of patients and/or prospective patient's teeth may be utilized to track progress of a patient's dental treatment and/or determine whether the dental treatment will work on a prospective patient. Sending photos to an orthodontist or other practitioner can obfuscate the need for repeated visits to an orthodontist.

However, the process of taking photographs of a patient's teeth can be cumbersome without assistance. For instance, a patient may require an additional person to assist them in taking clear photographs of that patient's teeth at different times during the dental treatment. Further, the distances and angles from the teeth of the patient may vary by image, resulting in inconsistencies between consecutive images and/or inconsistencies in images between different periods of the dental treatment process.

BRIEF DESCRIPTION OF THE DRAWINGS

FIG. 1D illustrates perspective views of a first portion and a second portion of an adjustable cheek retractor according to a number of embodiments of the present disclosure.

FIG. 1E illustrates perspective views of a first portion of an adjustable cheek retractor, an upper portion of a lip holder and a bottom portion of a lip holder of an adjustable cheek retractor according to a number of embodiments of the present disclosure.

FIG. 1F illustrates perspective views of an adjustable cheek retractor according to a number of embodiments of the present disclosure.

FIG. 2A illustrates a front view of a cheek retractor and a side view of a mobile device holder according to a number of embodiments of the present disclosure.

FIG. 2B illustrates a front view of a mobile device holder according to a number of embodiments of the present disclosure.

FIG. 3 illustrates a front view of a mobile device holder according to a number of embodiments of the present disclosure.

FIG. 4 illustrates a front view of a mobile device holder according to a number of embodiments of the present disclosure.

DETAILED DESCRIPTION

Figure 1A:
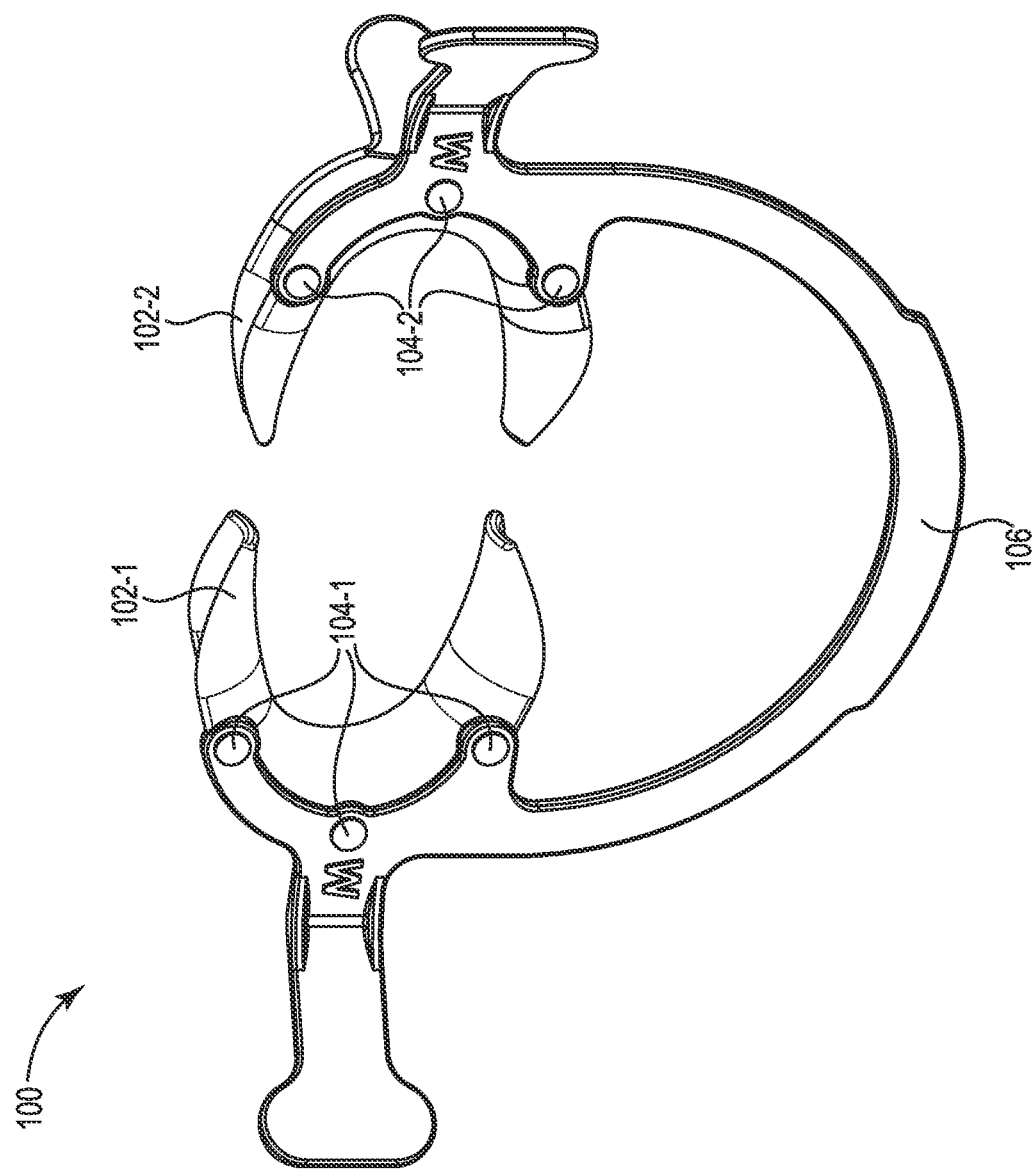
FIG. 1A illustrates a perspective view of a cheek retractor according to a number of embodiments of the present disclosure.

The present disclosure provides computing device readable medium, devices, and systems that utilize a cheek retractor and/or a mobile device holder for case assessment and/or dental treatments. Such solutions may simplify taking images of teeth of patients and/or prospective patients. Further, the images may include more consistent distances and/or angles from patients' teeth, allowing for more accurate scaling and rendering than images with inconsistent distances and/or angles from patients' teeth. The images can be more useful for progress tracking for current patients and/or determining whether various dental treatments will work on prospective patients.

In the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. For example, 104 may reference element "04" in FIG. 1A, and a similar element may be referenced as 204 in FIG. 2.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present disclosure, and should not be taken in a limiting sense.

FIG. 1A illustrates a perspective view of a cheek retractor according to a number of embodiments of the present disclosure. Cheek retractor 100 can include first lip holder 102-1, second lip holder 102-2, first imaging markers 104-1, second imaging markers 104-2, and bridge 106.

First lip holder 102-1 and second lip holder 102-2 can be shaped to fit into a user's mouth. As used herein, a user can include a patient and/or a prospective patient. The first lip holder 102-1 and second lip holder 102-2 can be of a "C" shape such that the first lip holder 102-1 and second lip holder 102-2 can follow the contour of the user's mouth and lips. The first lip holder 102-1 and second lip holder 102-2 can include a trough to receive the lips of the user. When inserted into the mouth of the user, the first lip holder 102-1 and second lip holder 102-2 are configured to hold the cheek of the user away from the user's mouth to expose the teeth of the user.

Cheek retractor 100 can include a bridge 106. Bridge 106 can connect the first lip holder 102-1 and second lip holder 102-2. Bridge 106 can be shaped to provide force to hold the cheek of the user away from the mouth of the user to expose the teeth of the user.

The first lip holder 102-1, second lip holder 102-2, and bridge 106 can be manufactured from material such as a plastic or other composite to provide the required force to hold the cheek of the user away from the user's mouth to expose the teeth of the user. The material can withstand sterilization techniques, including cold sterilization methods. The first lip holder 102-1, second lip holder 102-2, and bridge 106 can be manufactured from a material that is biocompatible such that it is not irritating to the user's oral mucosa and skin when inserted into the mouth of the user.

Cheek retractor 100 can be manufactured, in some examples, by downloading a computer-aided design (CAD) virtual model to a rapid prototyping process, such as, for example, a computer-aided manufacturing (CAM) milling, stereolithography, and/or photolithography process. In some examples, cheek retractor 100 can be manufactured via overmolding, injection molding, a rapid prototyping machine or direct fabrication device, such as a SLA or 3D printing machine, to form and/or create cheek retractor 100, among other manufacturing techniques and/or processes.

The first lip holder 102-1 can include first imaging markers 104-1. Each of the first imaging markers 104-1 can be located a predefined distance from the remaining first imaging markers 104-1. For example, as shown in FIG. 1A, the top imaging marker of the first imaging markers 104-1 can be located 2.3 centimeters (cm) from the middle imaging marker of the first imaging markers 104-1, and the middle imaging marker of the first imaging markers 104-1 can be located 2.3 cm from the bottom imaging marker of the first imaging markers 104-1, although embodiments of the present disclosure are not limited to the imaging markers being located 2.3 cm from each other. The top imaging marker of the first imaging markers 104-1 can be located 3.7 cm from the bottom imaging marker of the first imaging markers 104-1, although embodiments of the present disclosure are not limited to the top and the bottom imaging markers being located 3.7 cm from each other.

The second lip holder 102-2 can include second imaging markers 104-2. Each of the second imaging markers 104-2 can be located a predefined distance from the remaining second imaging markers 104-2. For example, as shown in FIG. 1A, the top imaging marker of the second imaging markers 104-2 can be located 2.3 centimeters (cm) from the middle imaging marker of the second imaging markers 104-2, and the middle imaging marker of the second imaging markers 104-2 can be located 2.3 cm from the bottom imaging marker of the second imaging markers 104-2, although embodiments of the present disclosure are not limited to the imaging markers being located 2.3 cm from each other. The top imaging marker of the second imaging markers 104-2 can be located 3.7 cm from the bottom imaging marker of the second imaging markers 104-2, although embodiments of the present disclosure are not limited to the top and the bottom imaging markers being located 3.7 cm from each other.

The first imaging markers 104-1 and the second imaging markers 104-2 (referred to collectively as imaging markers 104) can be a predetermined size and configured to determine the scale of the teeth of the user. For example, a computing device can receive images of the teeth of the user exposed by cheek retractor 100, where the images include the first imaging markers 104-1 and the second imaging markers 104-2. The computing device can utilize the predetermined size of the first imaging markers 104-1 and the second imaging markers 104-2 and the predefined distances between them to determine a scale of the teeth of the user by equating the predefined distances between the first imaging markers 104-1 and the second imaging markers 104-2 to a number of pixels in the images, as will be further described herein with respect to FIG. 6.

In some embodiments, the first imaging markers 104-1 and the second imaging markers 104-2 can be on a same plane with respect to each other in three-dimensional (3D) space. For example, the first imaging markers 104-1 can be in a same plane, and the second imaging markers 104-2 can be in a same plane. The plane of the first imaging markers 104-1 and the plane of the second imaging markers 104-1 can be the same plane or can be different planes. In some embodiments, the first imaging markers 104-1 can be located at different angles with respect to each other, and the second imaging markers 104-2 can be located at different angles with respect to each other. The scale of the teeth of the user may be determined using the predefined distances of the imaging markers 104, the predetermined size of the imaging markers 104, the planes of the imaging markers 104, and/or the angles of imaging markers 104. The scale of the teeth may be determined in 3D space using, for example, an X, Y, and/or Z coordinate system.

The first imaging markers 104-1 and the second imaging markers 104-2 can be a paper material, although embodiments of the present disclosure are not limited to a paper material. In some examples, the first imaging markers 104-1 and the second imaging markers 104-2 can be included on cheek retractor 100 during an overmolding and/or injection molding process, among other manufacturing techniques and/or processes. In some examples, the first imaging markers 104-1 and the second imaging markers 104-2 can be included on cheek retractor 100 by being stuck on (e.g., imaging markers 104 can be stickers placed on cheek retractor 100).

As shown in FIG. 1A, first lip holder 102-1 includes three first imaging markers 104-1 and second lip holder 102-2 includes three second imaging markers 104-2. Having three imaging markers can provide a more accurate scale of the user's teeth as compared to using less than three imaging markers, as well as providing more accurate reference points when combining multiple images of the user's teeth than using less than three imaging markers, as will be further described herein with respect to FIG. 6.

Although described herein and shown in FIG. 1A as first lip holder 102-1 including three imaging markers and second lip holder 102-2 including three imaging markers, embodiments of the present disclosure are not so limited. For example, first lip holder 102-1 can include more than three imaging markers, and second lip holder 102-2 can include more than three imaging markers.

The first imaging markers 104-1 and the second imaging markers 104-2 can be colored, and include one color or multiple colors. In some examples, cheek retractor 100 can be colored (e.g., green), and the first imaging markers 104-1 and the second imaging markers 104-2 can be a single solid color (e.g., orange). In some examples, cheek retractor 100 can be transparent, and the first imaging markers 104-1 and the second imaging markers 104-2 can be a multiple colors (e.g., orange with a secondary blue or green circle). Utilizing orange and/or orange with secondary blue or green imaging markers can provide a color contrast in images relative to other colored imaging markers, although embodiments of the present disclosure are not limited to orange and/or orange/blue/green color combinations.

The first imaging markers 104-1 and the second imaging markers 104-2 can be circular. However, embodiments of the present disclosure are not limited to circular imaging markers. For example, the first imaging markers 104-1 and the second imaging markers 104-2 can be other shapes, including squares, rectangles, etc., as well as other irregular shapes (e.g., a circle with a portion of the circle removed), etc.

Cheek retractor 100 can be used by a user to take images (e.g., photograph(s) and/or video) of the user's teeth. The images can include the first imaging markers 104-1 and the second imaging markers 104-2 which may be used to determine a scale of the user's teeth. Utilizing the images of and the scale of the user's teeth, a computing device may generate a model of the user's teeth, as will be further described herein with respect to FIG. 6. The model may be a two-dimensional (2D) and/or a three-dimensional (3D) model.

The model may be used, in some examples, to determine whether a user's teeth are suitable for a particular dental procedure (e.g., case assessment). For example, a treatment professional can review the model to determine a severity of a patient's malocclusion (e.g., mild, moderate, etc.), a type of dental procedure and associated dental appliances that would be suitable for fixing the particular malocclusion, and/or an amount of time needed to fix the particular malocclusion, among other factors.

The model may be used, in some examples, to track the progress of an ongoing dental procedure for a particular user. The model generated from the images can be compared to a predefined model of the user's teeth to track the progress of the ongoing dental procedure. For example, a treatment professional can review the model and compare it to a predefined model that may have been generated at the onset of the dental procedure to determine whether the dental procedure is proceeding as anticipated. The treatment professional can continue the dental procedure for the user if the dental procedure is proceeding as anticipated. Additionally, the treatment professional may make alterations to the dental procedure in the event the dental procedure is not proceeding as anticipated.

The cheek retractor including the imaging markers can assist in generating an accurate model of the user's teeth. The model can allow a treatment professional to determine whether a user's teeth are suitable for a particular dental procedure and/or to track an ongoing dental procedure. The treatment professional can utilize the model to help make this determination without the user having to make a time consuming visit the treatment professional, saving both the user and the treatment professional time and money.

Figure 1B:
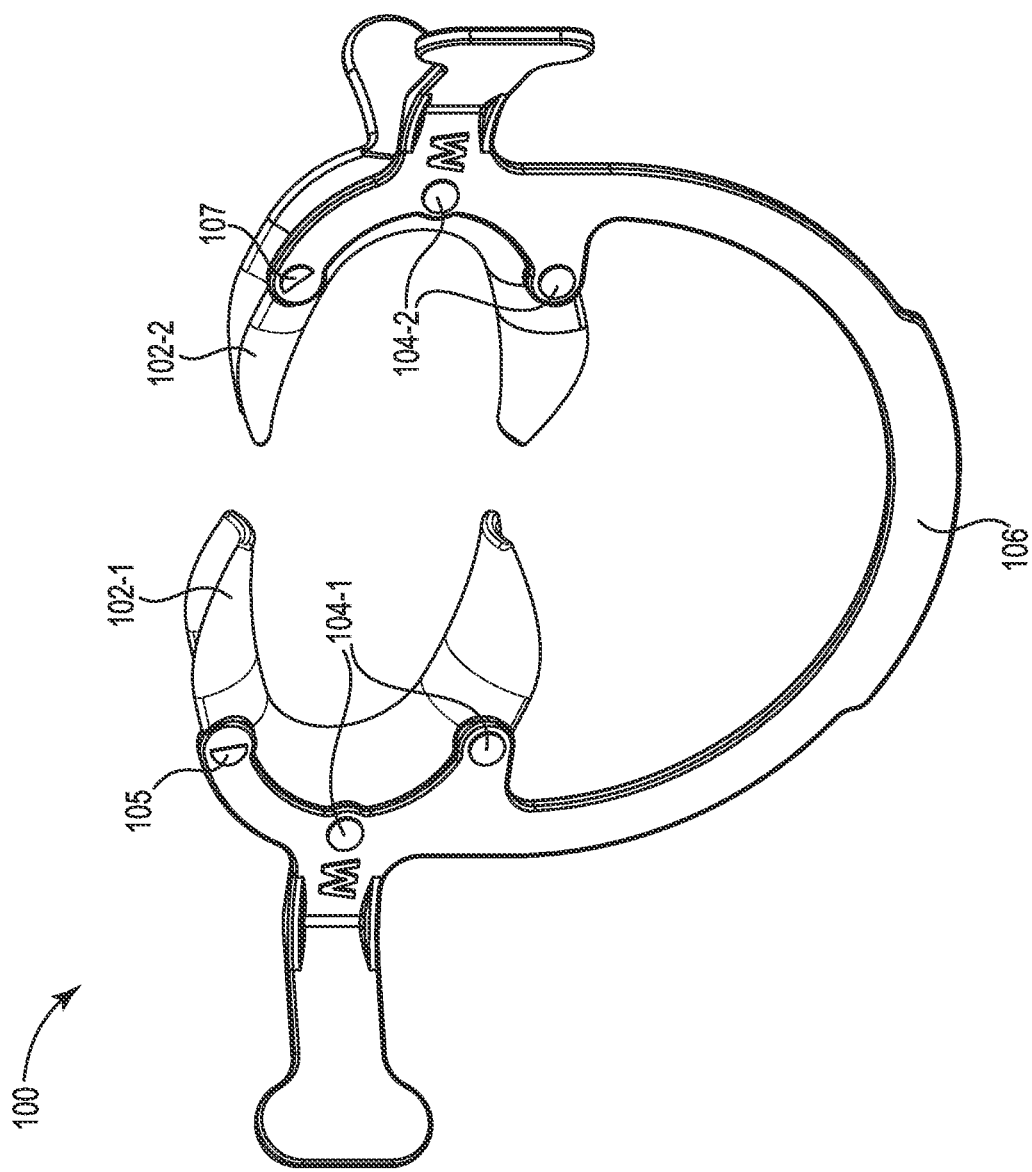
FIG. 1B illustrates a perspective view of a cheek retractor according to a number of embodiments of the present disclosure.

FIG. 1B illustrates a perspective view of a cheek retractor according to a number of embodiments of the present disclosure. As previously described in connection with FIG. 1A, cheek retractor 100 can include first lip holder 102-1, second lip holder 102-2, first imaging markers 104-1, second imaging markers 104-2, and bridge 106. Cheek retractor 100 can further include sizing imaging marker 105 and sizing imaging marker 107.

The first lip holder 102-1 can include first imaging markers 104-1 and sizing imaging marker 105. Each of the first imaging markers 104-1 and sizing imaging marker 105 can be located a predefined distance from each other. For example, as shown in FIG. 1B, sizing imaging marker 105 can be located 2.3 centimeters (cm) from the middle-left imaging marker of the first imaging markers 104-1, and the middle-left imaging marker of the first imaging markers 104-1 can be located 2.3 cm from the bottom imaging marker of the first imaging markers 104-1, although embodiments of the present disclosure are not limited to the imaging markers being located 2.3 cm from each other. Sizing imaging marker 105 can be located 3.7 cm from the bottom imaging marker of the first imaging markers 104-1, although embodiments of the present disclosure are not limited to sizing imaging marker 105 and the bottom imaging marker of the first imaging markers 104-1 being located 3.7 cm from each other.

The second lip holder 102-2 can include second imaging markers 104-2 and sizing imaging marker 107. Each of the second imaging markers 104-2 and sizing imaging marker 107 can be located a predefined distance from the remaining second imaging markers 104-2. For example, as shown in FIG. 1B, sizing imaging marker 107 can be located 2.3 centimeters (cm) from the middle-right imaging marker of the second imaging markers 104-2, and the middle-right imaging marker of the second imaging markers 104-2 can be located 2.3 cm from the bottom imaging marker of the second imaging markers 104-2, although embodiments of the present disclosure are not limited to the imaging markers being located 2.3 cm from each other. Sizing imaging marker 107 can be located 3.7 cm from the bottom imaging marker of the second imaging markers 104-2, although embodiments of the present disclosure are not limited to the sizing imaging marker 107 and the bottom imaging marker of the second imaging markers 104-2 being located 3.7 cm from each other.

As previously described in connection with FIG. 1A, first imaging markers 104-1 and second imaging markers 104-2, as well as sizing imaging marker 105 and sizing imaging marker 107 can be a predetermined size and used to determine the scale of the teeth of the user. For example, a computing device can receive images of the teeth of the user exposed by cheek retractor 100, where the images include the first imaging markers 104-1, sizing imaging marker 105, the second imaging markers 104-2, and sizing imaging marker 107. The computing device can utilize the predetermined size of first imaging markers 104-1, sizing imaging marker 105, the second imaging markers 104-2, and sizing imaging marker 107 and the predefined distances between them to determine a scale of the teeth of the user by equating the predefined distances between first imaging markers 104-1, sizing imaging marker 105, the second imaging markers 104-2, and sizing imaging marker 107 to a number of pixels in the images, as will be further described herein with respect to FIG. 6.

Sizing imaging marker 105 and sizing imaging marker 107 can be used to determine a size of cheek retractor 100. The size of cheek retractor 100 can correspond to a size of a patient's mouth. For example, a first patient may have a mouth size corresponding to a large sized cheek retractor 100, while a second patient may have a mouth size corresponding to a medium sized cheek retractor 100. Cheek retractor 100 sizes may vary from small, medium, large, extra-large, etc. Additionally, cheek retractor 100 sizes may include sizes from less than small to larger than extra-large.

Sizing imaging marker 105 and sizing imaging marker 107 can include shapes and/or orientations that correspond to the size of cheek retractor 100. For example, as illustrated in FIG. 1B, sizing imaging marker 105 is a half-circle shape, where the half-circle portion of the imaging marker is oriented vertically and on a left side of a sizing imaging marker location on cheek retractor 100 as viewed from the perspective illustrated in FIG. 1B. The left and vertically oriented sizing imaging marker 105 can correspond to a medium sized cheek retractor 100. As another example, as illustrated in FIG. 1B, sizing imaging marker 107 is a half circle shape, where the half-circle portion of the imaging marker is oriented horizontally and on a top side of a sizing imaging marker location on cheek retractor 100 as viewed from the perspective illustrated in FIG. 1B. The top and horizontally oriented sizing imaging marker 107 can correspond to a large sized cheek retractor 100.

In some examples, a combination of the orientation and placement of sizing imaging markers 105, 107 can correspond to the size of cheek retractor 100. For example, the left and vertically oriented sizing imaging marker 105 and the top and horizontally oriented sizing imaging marker 107 can correspond to a medium sized cheek retractor 100. As another example, a right and vertically oriented sizing imaging marker 105 and a bottom and horizontally oriented sizing imaging marker 107 can correspond to a large sized cheek retractor 100, among other combinations of the orientation and placement of sizing imaging markers 105, 107.

Although sizing imaging markers 105, 107 are illustrated in FIG. 1B and described above as being left and vertically oriented and top and horizontally oriented, respectively, embodiments of the present disclosure are not so limited. In some examples, sizing imaging marker 105 can be right and vertically oriented, top and horizontally oriented, bottom and horizontally oriented, oriented at an angle between 0 and 360°, etc. In some examples, sizing imaging marker 107 can be bottom and horizontally oriented, left and vertically oriented, right and vertically oriented, oriented at an angle between 0 and 360°, etc. In some examples, sizing imaging markers 105, 107 can be shapes other than a half-circle. For example, sizing imaging markers 105, 107 can be semi-circles (e.g., less than and/or greater than a half-circle shape), squares, rectangles, other irregular shapes (e.g., a circle with a portion of the circle removed), etc.

Sizing imaging markers 105, 107 can be a paper material, can be included on cheek retractor 100 during an overmolding and/or injection molding process, and/or can be stickers, similar to first imaging markers 104-1 and second imaging markers 104-2, as previously described in connection with FIG. 1A. Sizing imaging markers 105, 107 can be colored, and can include one color or multiple colors, similar to first imaging markers 104-1 and second imaging markers 104-2, as previously described in connection with FIG. 1A.

As previously described in connection with FIG. 1A, cheek retractor 100 can be used by a user to take images (e.g., photograph(s) and/or video) of the user's teeth. The images can include the first imaging markers 104-1 and the second imaging markers 104-2, as well as sizing imaging markers 105, 107, which may be used to determine a scale of the user's teeth and a size of cheek retractor 100. Utilizing the images of and the scale of the user's teeth and the size of cheek retractor 100, a computing device may generate a model of the user's teeth, as will be further described herein with respect to FIG. 6. The model may be a two-dimensional (2D) and/or a three-dimensional (3D) model. The model may be used to determine whether a user's teeth are suitable for a particular dental procedure, to track progress of an ongoing dental procedure, and/or assist in generating an accurate model of the user's teeth, among other uses, as previously described in connection with FIG. 1A.

Figure 1C:
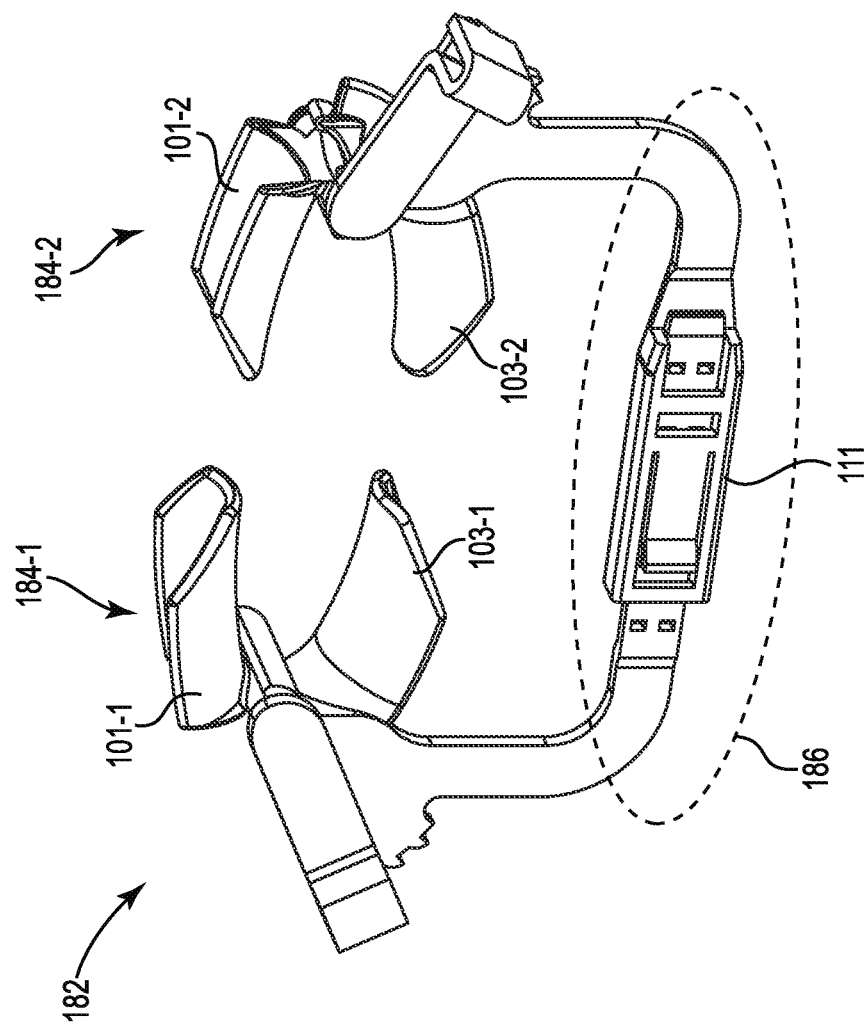
FIG. 1C illustrates a perspective view of an adjustable cheek retractor according to a number of embodiments of the present disclosure.

FIG. 1C illustrates a perspective view of an adjustable cheek retractor 182 according to a number of embodiments of the present disclosure. Adjustable cheek retractor 182 can include first lip holder 184-1, second lip holder 184-2, and bridge 186. First lip holder 184-1 can include upper portion 101-1 and bottom portion 103-1. Second lip holder 184-2 can include upper portion 101-2 and bottom portion 103-2.

First lip holder 184-1 and second lip holder 184-2 can be shaped to fit into a user's mouth. For example, the upper portion 101-1 and the bottom portion 103-1 of the first lip holder 184-1 can be of a "C" shape such that the upper portion 101-1 and the bottom portion 103-1 can follow the contour of the user's mouth and lips. Similarly, the upper portion 101-2 and the bottom portion 103-2 of the second lip holder 184-2 can be of a "C" shape such that the upper portion 101-2 and the bottom portion 103-2 can follow the contour of the user's mouth and lips.

The first lip holder 184-1 and the second lip holder 184-2 can be height adjustable. For example, the upper portion 101-1 can be connected to the bottom portion 103-1 of the first lip holder 184-1 at a hinge, the upper portion 101-2 can be connected to the bottom portion 103-2 of the second lip holder 184-2 at a hinge. The first lip holder 184-1 can be height adjustable about the hinge of first lip holder 184-1, and the second lip holder 184-2 can be height adjustable about the hinge of second lip holder 184-2, as is further described in connection with FIG. 1E.

Adjustable cheek retractor 182 can include a bridge 186. Bridge 186 can include a latch mechanism 111. The first lip holder 184-1 and the second lip holder 184-2 can be connected via the latch mechanism 111 of the bridge 186.

The width between the first lip holder 184-1 and the second lip holder 184-2 can be adjustable. For example, a first user may have a larger mouth than a second user; the width between first lip holder 184-1 and second lip holder 184-2 can be made to be larger in order for the first user to utilize adjustable cheek retractor 182 to hold a cheek away from the mouth of the first user in order to expose the teeth of the first user. The width between the first lip holder 184-1 and the second lip holder 184-2 can be adjustable via the latch mechanism 111, as is further described in connection with FIG. 1D.

Although not shown in FIG. 1C for clarity and so as not to obscure embodiments of the present disclosure, in some examples, the adjustable cheek retractor 182 can include imaging markers. For example, the first lip holder 184-1 can include first sizing imaging markers and the second lip holder 184-2 can include second sizing imaging markers. The imaging markers on the first lip holder 184-1 can be included on the upper portion 101-1, the bottom portion 103-1, and/or any combination thereof. Similarly, the imaging markers on the second lip holder 184-2 can be included on the upper portion 101-2, the bottom portion 103-2, and/or any combination thereof. The sizing imaging markers can correspond to a size of the adjustable cheek retractor 182.

FIG. 1D illustrates perspective views of a first portion 183 and a second portion 185 of an adjustable cheek retractor according to a number of embodiments of the present disclosure. The adjustable cheek retractor can include bottom portion 103-1 of the first lip holder and bottom portion 103-2 of the second lip holder, plurality of engagement apertures 113, latch 115, and engagement teeth 117 as illustrated in reverse view 187 of latch 115.

As previously described in connection with FIG. 1C, the adjustable cheek retractor can include a bridge connecting the first lip holder and the second lip holder. The bridge can include a latch mechanism. As illustrated in FIG. 1D, the latch mechanism can include a plurality of engagement apertures 113 and a latch 115.

An aperture can, for example, refer to an opening in the bridge. The plurality of engagement apertures 113 can engage with engagement teeth 117. For example, the width between first portion 183 and the second portion 185 of the adjustable cheek retractor can be adjustable via the plurality of engagement structures 113 and the latch 115 having the engagement teeth 117, as is further described herein.

The engagement teeth 117 can engage particular engagement apertures of the plurality of engagement apertures 113. An engagement tooth can, for example, refer to a projecting member that can engage a corresponding aperture. As illustrated in FIG. 1D, engagement teeth 117 can engage particular engagement apertures of the plurality of engagement apertures 113. For instance, engagement teeth 117 can engage a top particular engagement aperture and a bottom particular aperture of the plurality of engagement apertures 113 (e.g., as oriented in FIG. 1D) such that the first portion 183 and the second portion 185 of the adjustable cheek retractor are at a fixed width relative to each other, where the fixed width is based on the particular top and bottom apertures engaged by the engagement teeth 117.

The width between the first portion 183 and the second portion 185 of the adjustable cheek retractor can be adjusted by adjusting the particular engagement apertures the engagement teeth 117 engage. For example, the width can be increased or decreased by engagement teeth 117 engaging different particular engagement apertures of the plurality of engagement apertures 113.

As illustrated in FIG. 1D, the engagement teeth 117 can be angled. The angled engagement teeth 117 can allow for the width between the first portion 183 and the second portion 185 of the adjustable cheek retractor to be adjusted to be larger without lifting latch 115. For example, the angle of engagement teeth 117 can be oriented such that the first portion 183 and the second portion 185 can be pulled apart to increase the width between the first portion 183 and the second portion 185 without lifting latch 115. The angle can allow the engagement teeth 117 to slide to different particular apertures of the plurality of engagement apertures 113 to increase the width.

In an example in which the adjustable cheek retractor is placed in a patient's mouth, allowing the width of the adjustable cheek retractor to be increased without lifting the latch 115 can allow for a user (e.g., the patient, treatment professional, etc.) to increase the width against an opposing force generated by the patient's cheeks and mouth.

The width between the first portion 183 and the second portion 185 of the adjustable cheek retractor can be adjusted to be smaller by lifting latch 115 to allow the engagement teeth 117 to slide to engage different particular engagement structures. For instance, the angle of the engagement teeth 117 will not allow for movement of the first portion 183 and the second portion 185 of the adjustable cheek retractor without lifting the latch 115. Therefore, a user (e.g., the patient, treatment professional, etc.) can lift the latch 115 to allow for movement of the first portion 183 and the second portion 185 to narrow the width between the first portion 183 and the second portion 185 of the adjustable cheek retractor. At the desired width, the user can release the latch 115, allowing for engagement teeth 117 to engage with particular engagement apertures of the plurality of engagement apertures 113.

FIG. 1E illustrates perspective views of a first portion 189 of an adjustable cheek retractor, an upper portion 101-1 of a lip holder 184-1 and a bottom portion 103-1 of a lip holder 184-1 of an adjustable cheek retractor according to a number of embodiments of the present disclosure.

The adjustable cheek retractor can include a first portion 189 having a first lip holder 184-1. The first lip holder 184-1 can include an upper portion 101-1 of the first lip holder 184-1 and a bottom portion 103-1 of the first lip holder 184-1.

The first lip holder 184-1 can be height adjustable. For example, the height between the upper portion 101-1 and the bottom portion 103-1 can be adjusted. The first lip holder 184-1 can be height adjustable about a hinge 121 of the first lip holder 184-1 via a ratcheting mechanism 119, as is further described herein.

Although not illustrated in FIG. 1E for clarity and so as not to obscure examples of the disclosure, the adjustable cheek retractor can include a second lip holder having an upper portion and a bottom portion. The second lip holder can be height adjustable about a hinge of the second lip holder via a ratcheting mechanism of the second lip holder, similar to the first lip holder 184-1.

The first lip holder 184-1 can include an upper portion 101-1. As illustrated by perspective view 191 in FIG. 1E, shows the upper portion 101-1 of the first lip holder 184-1. Upper portion 101-1 can include a barrel 123 and an adjustment tooth 127.

The first lip holder 184-1 can also include a bottom portion 101-2. As illustrated by perspective view 193 in FIG. 1E, shows the bottom portion 103-1 of the first lip holder 184-1. Bottom portion 103-1 can include a channel 125 and a plurality of ratcheting teeth 129.

As previously described above, the first lip holder 184-1 can include hinge 121. Hinge 121 can be comprised of the barrel 123 and channel 125. For example, barrel 123 can fit into channel 125 to form hinge 121. The barrel 123 can fit into channel 125 via an interference fit, and barrel 123 can rotate in channel 125. In other words, the barrel 123 can rotate in channel 125 to adjust the height of the first lip holder 184-1 by causing the upper portion 101-1 to rotate relative to the bottom portion of 103-1, as is further described herein.

Upper portion 101-1 can be connected to the bottom portion 103-1 via the ratcheting mechanism 119 and the hinge 121. The first lip holder 184-1 can be height adjustable via the ratcheting mechanism 119.

As previously described above, the upper portion 101-1 can include an adjustment tooth 127 and the bottom portion 101-3 can include a plurality of ratcheting teeth 129. The adjustment tooth 127 can engage a particular ratcheting tooth of the plurality of ratcheting teeth 129 to form the ratcheting mechanism 119. For example, adjustment tooth 127 can engage a particular ratcheting tooth such that the upper portion 101-1 and the bottom portion 103-1 are at a fixed height relative to each other, where the fixed height is based on the particular ratcheting tooth of the plurality of ratcheting teeth 129 engaged by the adjustment tooth 127.

The first lip holder 184-1 can be height adjustable by the adjustment tooth engaging a different ratcheting tooth of the plurality of ratcheting teeth 129. For example, the height can be increased or decreased by the adjustment tooth 127 engaging a different particular ratcheting tooth of the plurality of ratcheting teeth 129.

As illustrated in FIG. 1E, the plurality of ratcheting teeth 129 can be angled. Additionally, the adjustment tooth 127 can be angled. The angled plurality of ratcheting teeth 129 and the angled adjustment tooth 127 can allow for the height between the upper portion 101-1 and the bottom portion 103-1 to be adjusted to be larger without lifting adjustment tooth 127. For example, the angles of the plurality of ratcheting teeth 129 and the adjustment tooth 127 can be oriented such that the upper portion 101-1 and the bottom portion 103-1 can be rotated away from each other to increase the height between the upper portion 101-1 and the bottom portion 103-1 without lifting adjustment tooth 127. The angles of the plurality of ratcheting teeth 129 and the adjustment tooth 127 can allow the adjustment tooth 127 to slide to different particular ratcheting teeth of the plurality of ratcheting teeth 129 to increase the height.

In an example in which the adjustable cheek retractor is placed in a patient's mouth, allowing the height of the adjustable cheek retractor to be increased without lifting the adjustment tooth 127 can allow for a user (e.g., the patient, treatment professional, etc.) to increase the height against an opposing force generated by the patient's cheeks and mouth.

The height between the upper portion 101-1 and the bottom portion 103-1 can be adjusted to be smaller by lifting adjustment tooth 127 to allow the upper portion 101-1 to rotate. For instance, the angle of the adjustment tooth 127 and the plurality of ratcheting teeth 129 will not allow for movement of the upper portion 101-1 relative to the bottom portion 103-1 without lifting adjustment tooth 127 clear of the plurality of ratcheting teeth 129. Therefore, a user (e.g., the patient, treatment professional, etc.) can lift adjustment tooth 127 to allow for the upper portion 101-1 to rotate towards the bottom portion 103-1 to decrease the height between the upper portion 101-1 and the bottom portion 103-1. At the desired height between the upper portion 101-1 and the bottom portion 103-1, the user can release the adjustment tooth 127, allowing for the adjustment tooth 127 to engage a particular ratcheting tooth of the plurality of ratcheting teeth 129.

Although not shown in FIG. 1E for clarity and so as not to obscure embodiments of the present disclosure, the second lip holder (e.g., second lip holder 184-2) can include an upper portion, a bottom portion, a hinge, and a ratcheting mechanism. The second lip holder can be height adjustable similar to first lip holder 184-1.

FIG. 1F illustrates perspective views 194 of an adjustable cheek retractor according to a number of embodiments of the present disclosure. The adjustable cheek retractor can include first lip holder 184-1, second lip holder 184-2, and bridge 186. Bridge 186 can include rotational ratcheting mechanism 199.

As illustrated in FIG. 1F, the adjustable cheek retractor can include bridge 186. Bridge 186 can include a rotational ratcheting mechanism 199. The first lip holder 184-1 and the second lip holder 184-2 can be connected via the rotational ratcheting mechanism 199 of bridge 186.

The width between the first lip holder 184-1 and the second lip holder 184-2 can be adjustable. For example, a first user may have a larger mouth than a second user; the width between first lip holder 184-1 and second lip holder 184-2 can be made to be larger in order for the first user to utilize the adjustable cheek retractor to hold a cheek away from the mouth of the first user in order to expose the teeth of the first user. The width between the first lip holder 184-1 and the second lip holder 184-2 can be adjustable via the rotational ratcheting mechanism 199.

The rotational ratcheting mechanism 199 can include an adjustment tooth 195 and a plurality of ratcheting teeth 197. The adjustment tooth 195 can engage a particular ratcheting tooth of the plurality of ratcheting teeth 197. For example, adjustment tooth 195 can engage a particular ratcheting tooth such that first lip holder 184-1 and second lip holder 184-2 are at a fixed width relative to each other, where the fixed width is based on the particular ratcheting tooth of the plurality of ratcheting teeth 197 engaged by the adjustment tooth 195.

The first lip holder 184-1 and the second lip holder 184-2 can be width adjustable by the adjustment tooth 195 engaging a different ratcheting tooth of the plurality of ratcheting teeth 197. For example, the width can be increased or decreased by the adjustment tooth 195 engaging a different particular ratcheting tooth of the plurality of ratcheting teeth 197.

As illustrated in FIG. 1F, the plurality of ratcheting teeth 197 can be curved. Additionally, the adjustment tooth 195 can be angled. The curved plurality of ratcheting teeth 197 and the angled adjustment tooth 195 can allow for the width between the first lip holder 184-1 and the second lip holder 184-2 to be adjusted to be larger without lifting adjustment tooth 195. For example, the curves of the plurality of ratcheting teeth 197 and the angle of the adjustment tooth 195 can be oriented such that the first lip holder 184-1 and the second lip holder 184-2 can be rotated away from each other to increase the width between the first lip holder 184-1 and the second lip holder 184-2 without lifting adjustment tooth 195. The curves of the plurality of ratcheting teeth 197 and the angle of the adjustment tooth 195 can allow the adjustment tooth 195 to slide to different particular ratcheting teeth of the plurality of ratcheting teeth 197 to increase the width.

In an example in which the adjustable cheek retractor is placed in a patient's mouth, allowing the width of the adjustable cheek retractor to be increased without lifting the adjustment tooth 195 can allow for a user (e.g., the patient, treatment professional, etc.) to increase the width against an opposing force generated by the patient's cheeks and mouth.

The width between the first lip holder 184-1 and the second lip holder 184-2 can be adjusted to be smaller. For example, the width between the first lip holder 184-1 and the second lip holder 184-2 can be adjusted to be smaller by pulling apart the cheek retractor at the rotational ratcheting mechanism 199, as is further described herein with respect to FIG. 1G.

Figure 1G:
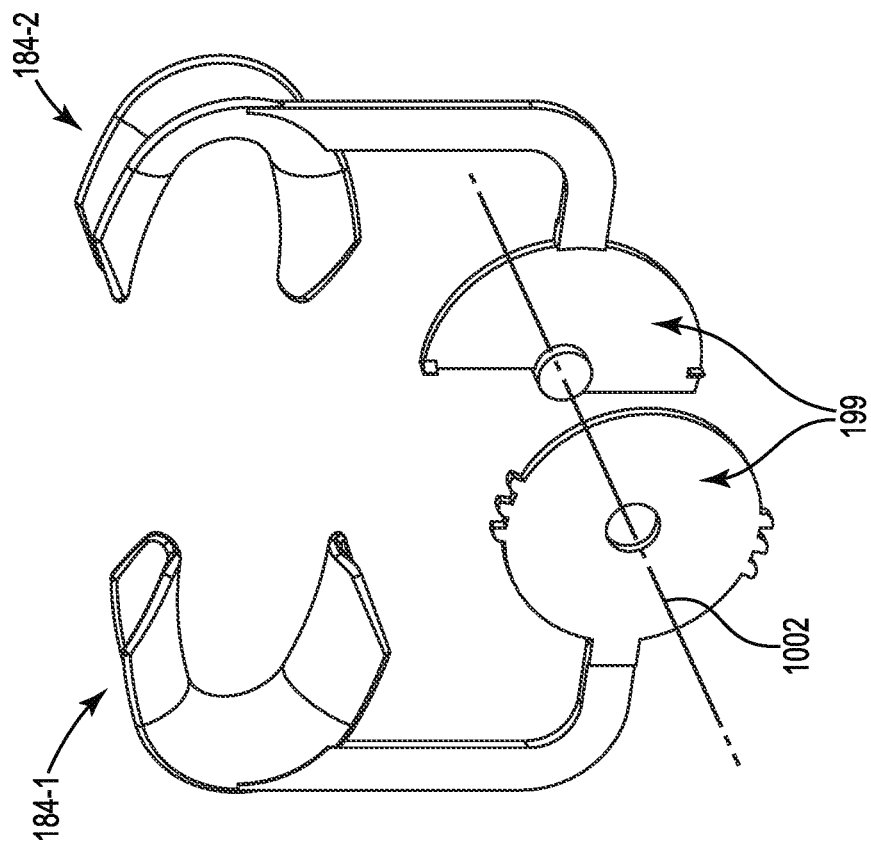
FIG. 1G illustrates perspective views of an adjustable cheek retractor having a pulled apart rotational ratcheting mechanism according to a number of embodiments of the present disclosure.

FIG. 1G illustrates perspective views 1000 of an adjustable cheek retractor having a pulled apart rotational ratcheting mechanism 199 according to a number of embodiments of the present disclosure. The adjustable cheek retractor can include first lip holder 184-1, second lip holder 184-2, and rotational ratcheting mechanism 199 aligned via central axis 1002.

The width between the first lip holder 184-1 and the second lip holder 184-2 can be adjusted to be smaller by pulling apart the rotational ratcheting mechanism 199. For example, rotational ratcheting mechanism 199, as illustrated in FIG. 1G, can be connected via a protrusion and an aperture aligned via central axis 1002. In some examples, protrusion can fit into the aperture via a mechanical fit and/or interference fit.

In order to adjust the width to be smaller, the rotational ratcheting mechanism 199 has to be pulled apart, as the angle of the adjustment tooth and the curves of the plurality of ratcheting teeth (e.g., adjustment tooth 195 and plurality of ratcheting teeth 197, previously described in connection with FIG. 1F) will not allow for movement of the first lip holder 184-1 relative to the second lip holder 184-2 without pulling apart the rotational ratcheting mechanism 199 so that the adjustment tooth is clear of the plurality of ratcheting teeth.

Therefore, a user (e.g., the patient, treatment professional, etc.) can pull apart rotational ratcheting mechanism 199 to allow for the first lip holder 184-1 and the second lip holder 184-2 to rotate towards each other to decrease the width between the first lip holder 184-1 and the second lip holder 184-2. At the desired width between the first lip holder 184-1 and the second lip holder 184-2, the user can connect the rotational ratcheting mechanism via central axis 1002, allowing for the adjustment tooth to engage a particular ratcheting tooth of the plurality of ratcheting teeth.

Figure 1H:
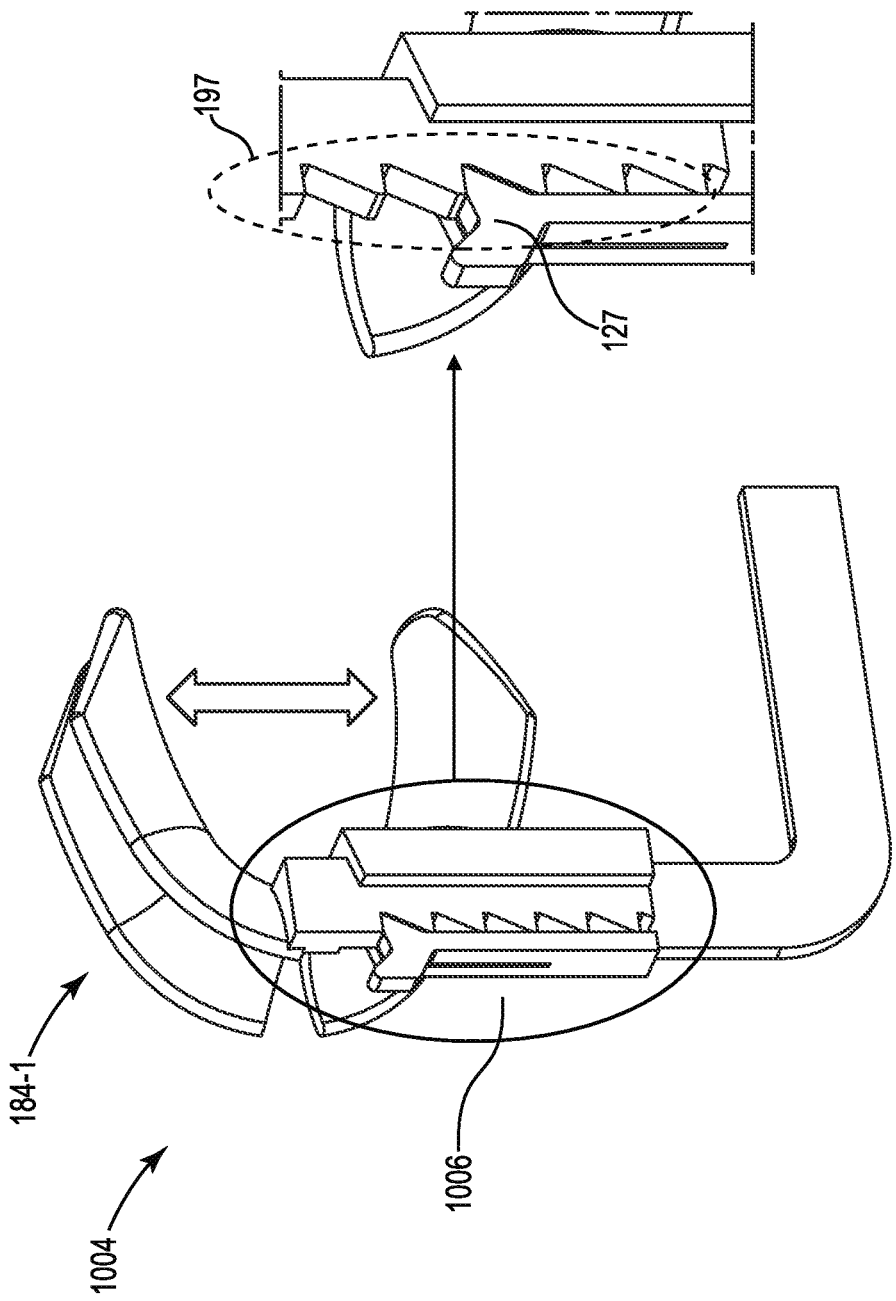
FIG. 1H illustrates perspective views of an adjustable cheek retractor according to a number of embodiments of the present disclosure.

FIG. 1H illustrates perspective views 1004 of an adjustable cheek retractor according to a number of embodiments of the present disclosure. The adjustable cheek retractor can include a first lip holder 184-1 and a linear ratcheting mechanism 1006. The linear ratcheting mechanism 1006 can include an adjustment tooth 195 and a plurality of ratcheting teeth 197.

The first lip holder 184-1 can be height adjustable. For example, the height between the upper portion and a bottom portion of first lip holder 184-1 can be adjusted. The first lip holder 184-1 can be height adjustable via a linear ratcheting mechanism 1006, as is further described herein.

Although not illustrated in FIG. 1H for clarity and so as not to obscure examples of the disclosure, the adjustable cheek retractor can include a second lip holder having an upper portion and a bottom portion. The second lip holder can be height adjustable about a linear ratcheting mechanism of the second lip holder, similar to the first lip holder 184-1.

The upper portion of first lip holder 184-1 can be connected to the bottom portion of first lip holder 184-1 via the linear ratcheting mechanism 1006. The first lip holder 184-1 can be height adjustable via the linear ratcheting mechanism 1006.

The linear ratcheting mechanism 1006 can include an adjustment tooth 195 and a plurality of ratcheting teeth 197. The adjustment tooth 195 can engage a particular ratcheting tooth of the plurality of ratcheting teeth 197 to form the linear ratcheting mechanism 1006. For example, adjustment tooth 195 can engage a particular ratcheting tooth such that the upper portion of first lip holder 184-1 and the bottom portion of first lip holder 184-1 are at a fixed height relative to each other, where the fixed height is based on the particular ratcheting tooth of the plurality of ratcheting teeth 197 engaged by the adjustment tooth 195.

The upper portion and bottom portions first lip holder 184-1 can be height adjustable relative to each other by the adjustment tooth 195 engaging a different ratcheting tooth of the plurality of ratcheting teeth 197. For example, the height can be increased or decreased by the adjustment tooth 195 engaging a different particular ratcheting tooth of the plurality of ratcheting teeth 197.

As illustrated in FIG. 1H, the plurality of ratcheting teeth 197 can be angled. Additionally, the adjustment tooth 195 can be angled. The angled plurality of ratcheting teeth 197 and the angled adjustment tooth 195 can allow for the height between the upper portion and the bottom portion to be adjusted to be larger without lifting adjustment tooth 195. For example, the angles of the plurality of ratcheting teeth 197 and the adjustment tooth 195 can be oriented such that the upper portion and the bottom portion can be moved linearly away from each other to increase the height between the upper portion and the bottom portion without lifting adjustment tooth 195. The angles of the plurality of ratcheting teeth 197 and the adjustment tooth 195 can allow the adjustment tooth 195 to slide to different particular ratcheting teeth of the plurality of ratcheting teeth 197 to increase the height.

In an example in which the adjustable cheek retractor is placed in a patient's mouth, allowing the height of the first lip holder 184-1 and/or the second lip holder (e.g., not illustrated in FIG. 1H) of the adjustable cheek retractor to be increased without lifting the adjustment tooth 195 can allow for a user (e.g., the patient, treatment professional, etc.) to increase the height against an opposing force generated by the patient's cheeks and mouth.

The height between the upper portion and the bottom portion can be adjusted to be smaller by pulling adjustment tooth 195 away from the plurality of ratcheting teeth 197 to allow the upper portion to slide towards the bottom portion of first lip holder 184-1. For instance, the angles of the adjustment tooth 195 and the plurality of ratcheting teeth 197 will not allow for movement of the upper portion relative to the bottom portion without pulling adjustment tooth 195 away from the plurality of ratcheting teeth 197. Therefore, a user (e.g., the patient, treatment professional, etc.) can pull adjustment tooth 195 away from the plurality of ratcheting teeth 197 to allow for the upper portion to move linearly towards the bottom portion of first lip holder 184-1 to decrease the height between the upper portion and the bottom portion of first lip holder 184-1. At the desired height between the upper portion and the bottom portion, the user can release the adjustment tooth 195, allowing for the adjustment tooth 195 to engage a particular ratcheting tooth of the plurality of ratcheting teeth 197.

Although not shown in FIG. 1H for clarity and so as not to obscure embodiments of the present disclosure, the second lip holder (e.g., second lip holder 184-2) can include an upper portion, a bottom portion, and a linear ratcheting mechanism. The second lip holder can be height adjustable similar to first lip holder 184-1.

FIG. 2A illustrates a front view of a cheek retractor and a side view of a mobile device holder according to a number of embodiments of the present disclosure. FIG. 2B illustrates a front view of a mobile device holder according to a number of embodiments of the present disclosure. In the embodiments of FIGS. 2A and 2B, the mobile device holder 208 includes an arm 210, an adjustment mechanism 212, and an attachment mechanism 214, where the arm 210 is configured to be attached to cheek retractor 200 (e.g., cheek retractor 100, previously described in connection with FIGS. 1A and 1B), where cheek retractor 200 includes first imaging markers 204-1 and second imaging markers 204-2 (e.g., first imaging markers 104-2 and second imaging markers 104-2, respectively, as previously described in connection with FIGS. 1A and 1B). Mobile device holder 208 further includes a base 216 configured to receive a mobile device 218, a vertical support mechanism 220, an attachment mechanism 222, and adjustable stops 224.

Arm 210 can include adjustment mechanism 212. As used herein, an adjustment mechanism refers to a mechanism allowing arm 210 to be adjusted relative to cheek retractor 200 such that at least one of photographs and video of teeth of the user may be taken by mobile device 218 at different positions relative to cheek retractor 200. In some examples, adjustment mechanism 212 can be a ball joint, although embodiments of the present disclosure are not limited to a ball joint. As used herein, a ball joint refers to a ball-and-socket joint allowing for free movement (e.g., rotation) in various planes. Adjustment mechanism 212 includes attachment mechanism 214. Arm 210 is configured to be attached to cheek retractor 200 via attachment mechanism 214, where cheek retractor 200 is configured to hold a cheek away from a mouth of a user to expose teeth of the user. Attachment mechanism 214 can be a clip, among other types of attachment mechanisms.

Base 216 is attached to arm 210. Base 216 can receive a mobile device 218. As used herein, a mobile device refers to a device including a user interface and a camera capable of taking photographs and/or video. The mobile device can include a camera on a same side of the mobile device as the user interface, and/or a camera on an opposite side of the mobile device of the user interface. As shown in FIGS. 2A and 2B, camera 240 and user interface 242 are on the same side of mobile device 218.

Base 216 can be movable relative to arm 210 such that a distance between mobile device 218 and the teeth of the user is configurable. For example, the base 216 may be slid forward and/or backwards to capture images of the user's teeth that may be required at various distances from the user's teeth, as will be further described herein. Base 216 may slide forward and/or backward on a track. The track may be a slot included in base 216 within which a portion of arm 210 is located, where the track may allow for movement of base 216 relative to arm 210.

The base 216 and/or arm 210 can include soft stops configured to inhibit (e.g., slightly inhibit) movement of base 216 relative to arm 210. As used herein, a soft stop may refer to material included base 216 and/or arm 210 to provide slight resistance to movement of the base 216 relative to arm 210. The soft stops can be located at predetermined locations along the axis of movement of base 216 relative to arm 210, where the predetermined locations can correspond to predefined distances from mobile device 218 to the teeth of the user. As shown in FIG. 2A, base 216 can include distance markings indicating to a user a distance from mobile device 218 to the teeth of the user. The distance markings can include an indicator marking a "correct" distance that may correspond to the distance needed for an image of the user's teeth that may be utilized for case assessment and/or progress tracking.

Mobile device holder 208 can include a vertical support mechanism 220, where the vertical support mechanism 220 includes a vertically adjustable attachment mechanism 222 configured to attach to mobile device 218. Vertically adjustable attachment mechanism 222 can slide up and/or down along an axis of movement defined by vertical support mechanism 220. Attachment mechanism 222 can be vertically adjusted to accommodate differently sized mobile devices 218. For example, attachment mechanism 222 can be slid up vertical support mechanism 220 to accommodate a first mobile device that is taller than a second, shorter mobile device.

Attachment mechanism 222 can prevent vertical movement of mobile device 218. For example, attachment mechanism 222 can prevent mobile device 218 from "tipping" forwards off of base 216.

In some examples, attachment mechanism 222 can be a suction cup. For example, the suction cup can create a vacuum in the suction cup to secure mobile device 218 in order to prevent movement of mobile device 218, such as a "tipping" movement, although embodiments of the present disclosure are not limited to a suction cup as attachment mechanism 222.

As shown in FIG. 2B, base 216 can include adjustable stops 224 configured to prevent lateral movement of mobile device 218. For example, adjustable stops 224 can provide a compressive force on mobile device 218 such that lateral movement (e.g., side-to-side movement) of mobile device 218 is prevented. Adjustable stops 224 can include a cover made of a rubber or other material that may provide friction to assist in preventing lateral movement of mobile device 218.

Adjustable stops 224 can be horizontally adjusted to accommodate differently sized mobile devices 218. For example, adjustable stops 224 can be adjusted sideways to accommodate a first mobile device that is wider than a second mobile device.

Arm 210, adjustment mechanism 212, attachment mechanism 214, base 216, vertical support mechanism 220, and adjustable stops 224 may be a plastic material or other polymer. Arm 210, adjustment mechanism 212, attachment mechanism 214, base 216, vertical support mechanism 220, and adjustable stops 224 may be manufactured from a plastic material or other polymer capable of withstanding the weight of mobile device 218. Arm 210, adjustment mechanism 212, attachment mechanism 214, base 216, vertical support mechanism 220, and adjustable stops 224 may be manufactured by downloading a computer-aided design (CAD) virtual model to a rapid prototyping process, such as, for example, a computer-aided manufacturing (CAM) milling, stereolithography, and/or photolithography process, overmolding, injection molding, and/or a rapid prototyping machine or direct fabrication device, such as a SLA or 3D printing machine, among other manufacturing techniques and/or processes.

Arm 210 can swivel about adjustment mechanism 212 such that an angle between mobile device 218 and the teeth of the user is configurable. Correspondingly, base 216, attached to arm 210, can swivel about adjustment mechanism 212. For example, arm 210 may be swiveled about adjustment mechanism 212 to capture images of the user's teeth that may be required at various angles from the user's teeth.

Mobile device 218 can take at least one of photographs and video of the teeth of the user at configurable distances via base 216 and/or configurable angles via adjustment mechanism 212. The photographs and/or video of the teeth can include at least one of the first imaging markers 204-1 and second imaging markers 204-2.

In some examples, user interface 242 of mobile device 218 can instruct a user to take a photograph of the user's teeth via camera 240, where the photograph is to be taken at a specified distance from the user's teeth. The user may adjust base 216 forwards or backwards so that the camera 240 included in mobile device 218 can take the photograph at the specified distance from the user's teeth, where the photograph includes at least one of the first imaging markers 204-1 and second imaging markers 204-2.

In some examples, user interface 242 of mobile device 218 can instruct a user to take a photograph of the user's teeth via camera 240, where the photograph is to be taken at a specified angle from the user's teeth. The user may adjust arm 210, and correspondingly base 216, by swiveling arm 210 about the adjustment mechanism 212 so that the camera 240 included in mobile device 218 can take the photograph at the specified angle from the user's teeth, where the photograph includes at least one of the first imaging markers 204-1 and second imaging markers 204-2.

The instructions to a user to take at least one of photographs and video of the teeth can be visual instructions via user interface 242, and/or can be audio instructions. In some examples, visual instructions can be presented to the user via user interface 242. In some examples, audio instructions can be broadcast to the user via an audio output of the mobile device, such as a speaker. In some examples, a combination of visual instructions via user interface 242 and audio instructions may be presented to the user.

Attaching mobile device holder 208 to cheek retractor 200 can allow a user to quickly and easily take images of the user's teeth at consistent angles and distances. The consistent images can allow for a more accurate model of the patient's teeth to be created, and accordingly a more accurate case assessment and/or more accurate progress tracking of the patient's dental procedure. Further, the mobile device holder 208 can allow the user to take the images of the user's teeth without the need for help from an additional person.

FIG. 3 illustrates a front view of a mobile device holder according to a number of embodiments of the present disclosure. In the embodiment of FIG. 3, the mobile device holder 330 includes a stand 332 and a base guide 336. The stand 332 can include stop mechanism 334. The base guide 336 can include position and angle markings 338-1, 338-2, 338-3 (referred to collectively as position and angle markings 338).

Stand 332 can be configured to receive a mobile device 318 (e.g., mobile device 118, 218, previously described in connection with FIGS. 1 and 2, respectively). Mobile device 318 can include a user interface 342 (e.g., user interface 242, previously described in connection with FIG. 2) and a camera 340 (e.g., camera 240, previously described in connection with FIG. 2) capable of taking photographs and/or video. Stand 332 may be configured such that it is able to be stood upright. For example, stand 332 may be curved or include members to allow stand 332 to be stood upright. Stand 332 can move relative to teeth of a user such that mobile device 318 can capture at least one of photographs and video of the user's teeth at at least one of various distances and angles from the user's teeth.

In some embodiments, stand 332 may be configured such that at least a portion of the stand 332 is folded. For example, a portion of stand 332 may be folded towards the position and angle markings 338 of the table guide 336 such that stand 332 is able to be stood upright.

Stand 332 can include stop mechanism 334. In some embodiments, stop mechanism 334 can be tabs that may be, for example, a portion of stand 332, although embodiments of the present disclosure are not so limited. Stop mechanism 334 can prevent movement of mobile device 318 with respect to stand 332. For example, stop mechanism 334 can prevent vertical movement of mobile device 318, such as a "tipping" movement.

Stand 332 can be a paper material such as cardboard. For example, stand 332 can be cardboard capable of being folded to receive mobile device 318. However, embodiments of the present disclosure are not limited to stand 332 being cardboard. For example, stand 332 can be plastic or any other material capable of being configured to stand upright and to receive mobile device 318.

Base guide 336 may be configured such that at least a portion of the base guide 336 is folded and the guide is configured into the base. The stand 332 may be located on base guide 336.

Base guide 336 can include at least one of different position and angle markings 338. The different position and angle markings 338 can correspond to predefined distances and/or angles indicating to a user a distance and/or an angle, respectively, from mobile device 318 to the teeth of the user.

Although shown in FIG. 3 as including base guide 336, embodiments of the present disclosure are not so limited. For example, stand 332 including mobile device 318 may be utilized without base guide 336 to capture at least one of photographs and video of a user's teeth at at least one of various distances and angles from the user's teeth.

Mobile device 318 is oriented on stand 332 such that camera 340 of mobile device 318 and user interface 342 of mobile device 318 face toward the position and angle markings 338 of base guide 336. Further, camera 340 of mobile device 318 and user interface 342 of mobile device 318 face toward the teeth of the user.

Mobile device 318 can take at least one of photographs and video of teeth of the user at at least one of the different position and angle markings 338 of base guide 336. User interface 342 can instruct a user to take a photograph and/or video of the user's teeth at specified distances and/or angles from the user's teeth. The user may adjust stand 332 using base guide 336 so that camera 340 can take a photograph and/or a video of the user's teeth at the specified distances and/or angles. For example, user interface 342 can instruct the user to take photographs of the user's teeth at an angle specified by position and angle marking 338-1 and 338-3, as well as a photograph directly in front of the user at position and angle marking 338-2, where the photographs include at least one imaging marker (e.g., imaging markers 104, 204, previously described in connection with FIGS. 1 and 2, respectively) included on a cheek retractor (e.g., cheek retractor 100, 200, previously described in connection with FIGS. 1 and 2, respectively). The cheek retractor can be configured to hold a cheek away from a mouth of the user to expose the teeth of the user.

The instructions to a user to take at least one of photographs and video of the teeth can be visual instructions via user interface 342, and/or can be audio instructions. In some examples, visual instructions can be presented to the user via user interface 342. In some examples, audio instructions can be broadcast to the user via an audio output of the mobile device, such as a speaker. In some examples, a combination of visual instructions via user interface 342 and audio instructions may be presented to the user.

Mobile device holder 330 can allow a user to quickly and easily take images of the user's teeth at consistent angles and distances without the need for help from an additional person. Similar to the embodiment described in connection with FIG. 2, the consistent images can allow for a more accurate model of the patient's teeth to be created, and accordingly a more accurate case assessment and/or more accurate progress tracking of the patient's dental procedure. Further, using a cardboard stand and base guide can allow a treatment professional or other entity to send a cost effective mobile device holder to a user that is easy to ship, as well as providing a mobile device holder for the user that is easy to use and can be disassembled for compact storage.

FIG. 4 illustrates a front view of a mobile device holder according to a number of embodiments of the present disclosure. In the embodiment of FIG. 4, the mobile device holder 444 includes a stand 432 (e.g., stand 332, previously described in connection with FIG. 3), a stand attachment 450, and a base guide 436 (e.g., base guide 336, previously described in connection with FIG. 3). The stand 432 can include stop mechanism 434 and a slot 446. The stand attachment 450 can include a tongue 448 and a reflective surface 452. The base guide 436 can include position and angle markings 438-1, 438-2, 438-3 (referred to collectively as position and angle markings 438), (e.g., position and angle markings 338, previously described in connection with FIG. 3).

Similar to the embodiment of FIG. 3, stand 432 may be configured such that it is able to be stood upright. For example, stand 432 may be curved or include members to allow stand 432 to be stood upright. In some examples, a portion of stand 432 may be folded towards the position and angle markings 438 of the base guide 436 such that stand 432 is able to be stood upright. Stand 432 can move relative to teeth of a user such that mobile device 418 can capture at least one of photographs and video of the user's teeth at at least one of various distances and angles from the user's teeth.

Stand 432 can be configured to receive a mobile device 418 (e.g., mobile device 118, 218, 318, previously described in connection with FIGS. 1-3, respectively). Mobile device 418 can include a user interface and a camera 451 capable of taking photographs and/or video.

Stand 432 can include stop mechanism 434. In some embodiments, stop mechanism 434 can be tabs that may be, for example, a portion of stand 432, although embodiments of the present disclosure are not so limited. Stop mechanism 434 can prevent movement of mobile device 418 with respect to stand 432. For example, stop mechanism 434 can prevent vertical movement of mobile device 418, such as a "tipping" movement.

Stand 432 can be a paper material such as cardboard. For example, stand 432 can be cardboard capable of being folded to receive mobile device 418. However, embodiments of the present disclosure are not limited to stand 432 being cardboard. For example, stand 432 can be plastic any other material capable of being configured to stand upright and to receive mobile device 418.

Base guide 436 may be configured such that at least a portion of the base guide 436 is folded and the guide is configured into the base. The stand 432 may be located on base guide 436.

Base guide 436 can include at least one of different position and angle markings 438. The different position and angle markings 438 can correspond to predefined distances and/or angles indicating to a user a distance and/or an angle, respectively, from mobile device 418 to the teeth of the user.

Although shown in FIG. 4 as including base guide 436, embodiments of the present disclosure are not so limited. For example, stand 432 including mobile device 418 may be utilized without base guide 436 to capture at least one of photographs and video of a user's teeth at at least one of various distances and angles from the user's teeth.

Stand 432 includes a slot 446 configured to receive a tongue 448 of stand attachment 450. For example, tongue 448 of stand attachment 450 can be slid into slot 446 of stand 432 such that stand attachment 450 is attached to stand 432.

Stand attachment 450 can be a paper material such as cardboard, among other types of paper materials. For example, stand attachment 450 can be cardboard capable of being folded such that tongue 448 can be slid into slot 446 of stand 432 to attach stand attachment 450 to stand 432.

A portion of stand attachment 450 can include a reflective surface 452. As used herein, a reflective surface refers to a surface from which light in an incoming direction is redirected to an outgoing direction. Reflective surface 452 can allow a user to see a reflection of the user interface of mobile device 418 when looking at reflective surface 452. For example, the user interface of mobile device 418 can instruct the user to take the photographs and/or video of the user's teeth at different positions and angles (as is further described herein with respect to FIG. 6). Reflective surface 452 can assist the user in taking at least one of photographs and video of the user's teeth at the different position and angle markings 438 by reflecting the user interface of mobile device 418 so that the user can position camera 451 in a correct position relative to the user's mouth/teeth for camera 451 to capture the photographs and/or video of the user's teeth at the correct positions and angles. Reflecting the user interface of mobile device 418 may be useful in assisting in capturing the photographs and/or video of teeth of a user who may be hearing impaired. Reflective surface 452 can be a glass material, a reflective metal (e.g., aluminum, etc.), and/or reflective fabric, among other reflective materials.

The instructions to a user to take at least one of photographs and video of the teeth can be visual instructions via user interface reflected off of reflective surface 452, and/or can be audio instructions. In some examples, visual instructions can be presented to the user via a user interface reflected off of reflective surface 452. In some examples, audio instructions can be broadcast to the user via an audio output of the mobile device, such as a speaker. In some examples, a combination of visual instructions via a user interface reflected off of reflective surface 452 and audio instructions may be presented to the user.

Mobile device 418 is oriented on stand 432 such that camera 451 of mobile device 418 faces towards the position and angle markings 438 of base guide 436 and a user interface of mobile device 418 faces away from the position and angle markings 438 of base guide 436. The user interface of mobile device 418 can be reflected off of reflective surface 452 of stand attachment 450.

Mobile device 418 can take at least one of photographs and video of teeth of the user at at least one of the different position and angle markings 438 of base guide 436. User interface can instruct a user, via reflective surface 452, to take a photograph and/or video of the user's teeth at specified distances and/or angles from the user's teeth (e.g., instructions from the user interface are reflected off reflective surface 452). The user may adjust stand 432, including stand attachment 450, using base guide 436 so that camera 451 can take a photograph and/or a video of the user's teeth at the specified distances and/or angles. For example, the user interface can instruct the user to take photographs of the user's teeth at an angle specified by position and angle marking 438-1 and 438-3, as well as a photograph directly in front of the user at position and angle marking 438-2, where the photographs include at least one imaging marker (e.g., imaging markers 104, 204, previously described in connection with FIGS. 1 and 2, respectively) included on a cheek retractor (e.g., cheek retractor 100, 200, previously described in connection with FIGS. 1 and 2, respectively). The cheek retractor can be configured to hold a cheek away from a mouth of the user to expose the teeth of the user.

Figure 5:
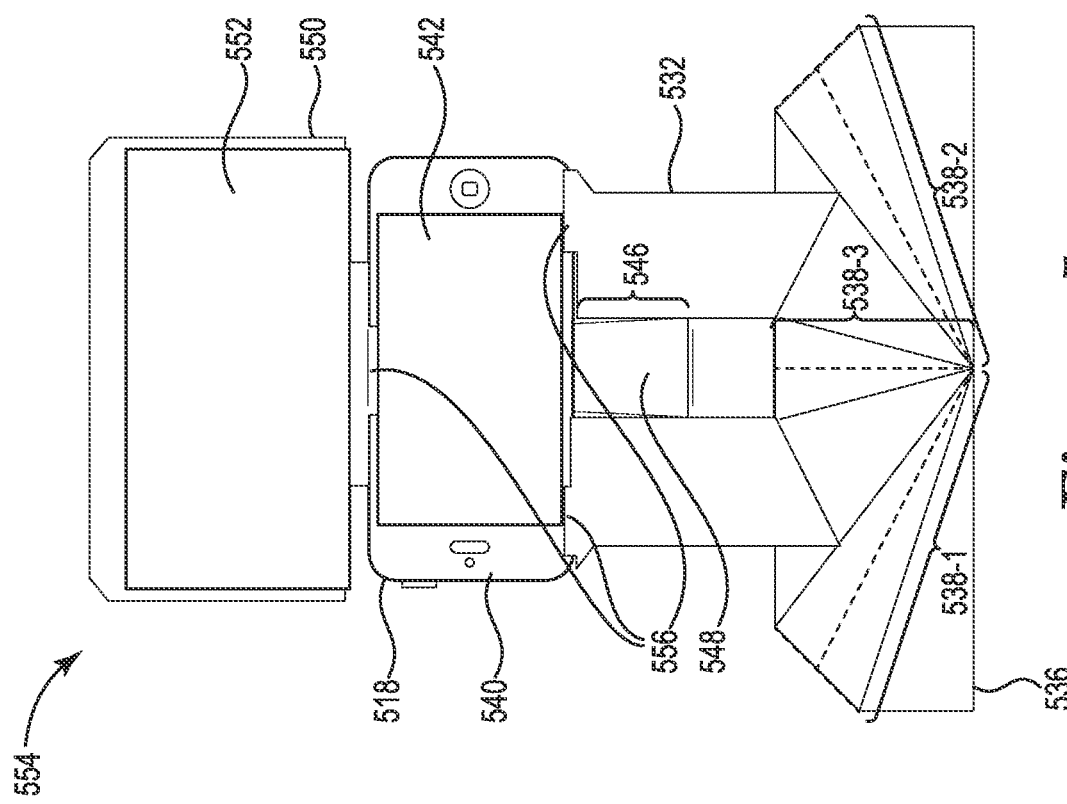
FIG. 5 illustrates a front view of a mobile device holder according to a number of embodiments of the present disclosure.

FIG. 5 illustrates a front view of a mobile device holder according to a number of embodiments of the present disclosure. In the embodiment of FIG. 5, the mobile device holder 554 includes a stand 532 (e.g., stand 332, 432, previously described in connection with FIGS. 3 and 4), a stand attachment 550 (e.g., stand attachment 450, previously described in connection with FIG. 4), and a base guide 536 (e.g., base guide 336, 436, previously described in connection with FIGS. 3 and 4). The stand 532 can include stop mechanism 556 and a slot 546 (e.g., slot 446, previously described in connection with FIG. 4). The stand attachment 550 can include a tongue 548 (e.g., tongue 448, previously described in connection with FIG. 4) and a reflective surface 552 (e.g., reflective surface 452, previously described in connection with FIG. 4). The base guide 536 can include position and angle markings 538-1, 538-2, 538-3 (referred to collectively as position and angle markings 538), (e.g., position and angle markings 338, 438, previously described in connection with FIGS. 3 and 4).

Similar to the embodiment of FIG. 4, stand 532 may be configured such that it is able to be stood upright. For example, stand 532 may be curved or include members to allow stand 532 to be stood upright. In some examples, a portion of stand 532 may be folded towards the position and angle markings 538 of the base guide 536 such that stand 532 is able to be stood upright. Stand 532 can move relative to teeth of a user such that mobile device 518 can capture at least one of photographs and video of the user's teeth at at least one of various distances and angles from the user's teeth.

Stand 532 can be configured to receive a mobile device 518 (e.g., mobile device 118, 218, 318, 418, previously described in connection with FIGS. 1-4, respectively). Mobile device 518 can include a user interface 542 (e.g., user interface 242, 342, previously described in connection with FIGS. 2 and 3) and a camera 540 (e.g., camera 240, 340, previously described in connection with FIGS. 2 and 3) capable of taking photographs and/or video.

Stand 532 can include stop mechanism 556. In some embodiments, stop mechanism 556 can be tabs that may be, for example, a portion of stand 532, although embodiments of the present disclosure are not so limited. Stop mechanism 556 can prevent movement of mobile device 518 with respect to stand 532. For example, stop mechanism 556 can prevent vertical movement of mobile device 518, such as a "tipping" movement.

Stand 532 can be a paper material such as cardboard. For example, stand 532 can be cardboard capable of being folded to receive mobile device 518. However, embodiments of the present disclosure are not limited to stand 532 being cardboard. For example, stand 532 can be plastic any other material capable of being configured to stand upright and to receive mobile device 518.

Base guide 536 is configured such that at least a portion of the base guide 536 is folded and the guide is configured into the base. The stand 532 may be located on base guide 536.

Base guide 536 can include at least one of different position and angle markings 538. The different position and angle markings 538 can correspond to predefined distances and/or angles indicating to a user a distance and/or an angle, respectively, from mobile device 518 to the teeth of the user.

Although shown in FIG. 5 as including base guide 536, embodiments of the present disclosure are not so limited. For example, stand 532 including mobile device 518 may be utilized without base guide 536 to capture at least one of photographs and video of a user's teeth at at least one of various distances and angles from the user's teeth.

Stand 532 includes a slot 546 configured to receive a tongue 548 of stand attachment 550. For example, tongue 548 of stand attachment 550 can be slid into slot 546 of stand 532 such that stand attachment 550 is attached to stand 532.

Stand attachment 550 can be a paper material such as cardboard, among other types of paper materials. For example, stand attachment 550 can be cardboard capable of being folded such that tongue 548 can be slid into slot 546 of stand 532 to attach stand attachment 550 to stand 532.

A portion of stand attachment 550 can include a reflective surface 552. For example, reflective surface 552 can allow a user to see themselves (e.g., their mouth and/or teeth) when looking at reflective surface 552.

Mobile device 518 is oriented on stand 532 such that camera 540 and user interface 542 of mobile device 518 face towards the position and angle markings 538 of base 536. Further, camera 540 of mobile device 518 and user interface 542 of mobile device 518 face toward the teeth of the user.

Mobile device 518 can take at least one of photographs and video of teeth of the user at at least one of the different position and angle markings 538 of base guide 536. User interface 542 can instruct a user to take a photograph and/or video of the user's teeth at specified distances and/or angles from the user's teeth. The user may adjust stand 532, including stand attachment 550, using base guide 536 so that camera 540 can take a photograph and/or a video of the user's teeth at the specified distances and/or angles. For example, the user interface can instruct the user to take photographs of the user's teeth at an angle specified by position and angle marking 538-1 and 538-3, as well as a photograph directly in front of the user at position and angle marking 538-2, where the photographs include at least one imaging marker (e.g., imaging markers 104, 204, previously described in connection with FIGS. 1 and 2, respectively) included on a cheek retractor (e.g., cheek retractor 100, 200, previously described in connection with FIGS. 1 and 2, respectively). The cheek retractor can be configured to hold a cheek away from a mouth of the user to expose the teeth of the user.

The instructions to a user to take at least one of photographs and video of the teeth can be visual instructions via user interface 542, and/or can be audio instructions. In some examples, visual instructions can be presented to the user via user interface 542. In some examples, audio instructions can be broadcast to the user via an audio output of the mobile device, such as a speaker. In some examples, a combination of visual instructions via user interface 542 and audio instructions may be presented to the user. The visual instructions to take at least one of photographs and video of the teeth can be carried out by the user and/or a treatment professional via the mobile device.

Figure 6:
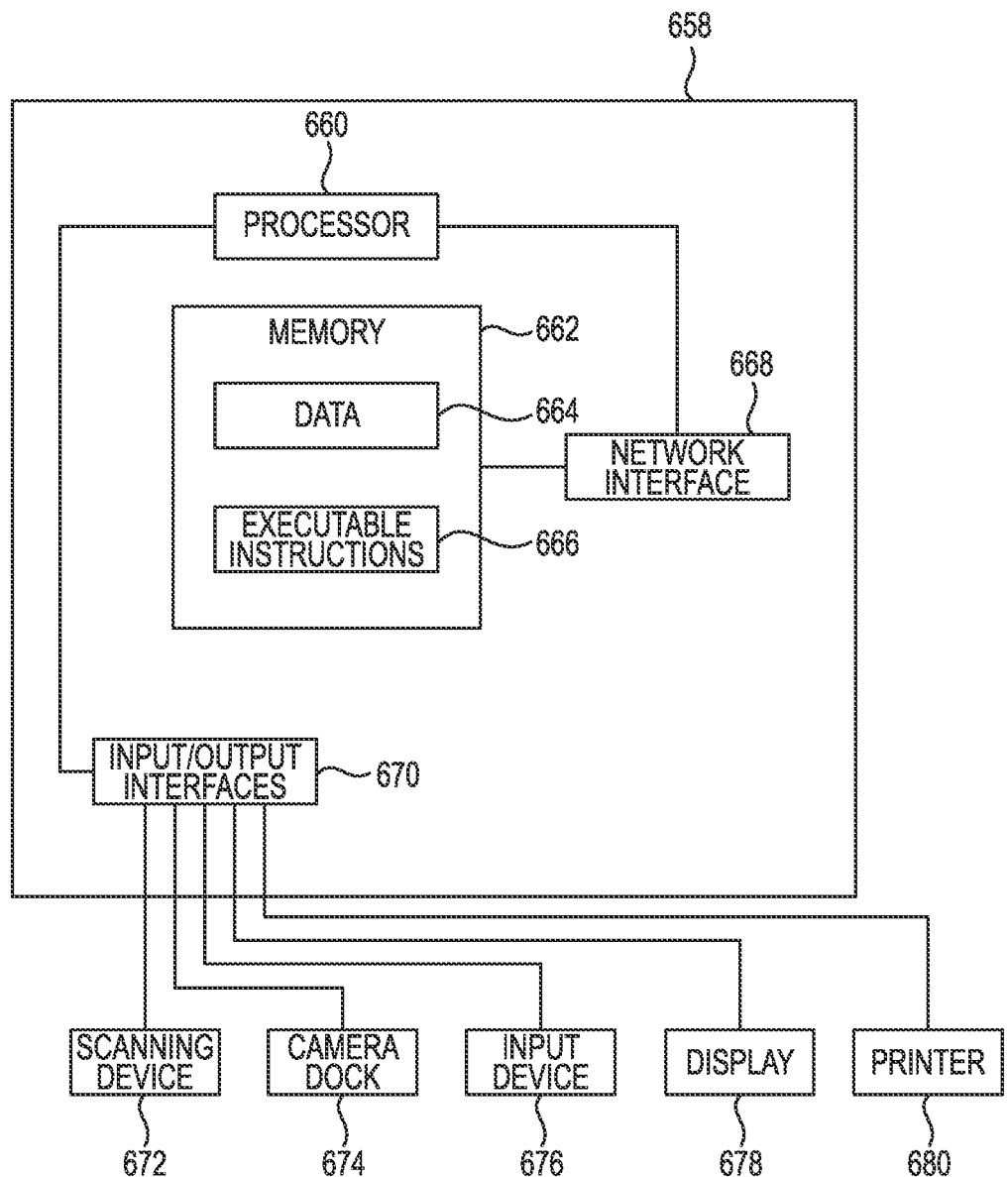
FIG. 6 illustrates a computing device that can be utilized according to one or more embodiments of the present disclosure.

FIG. 6 illustrates a computing device that can be utilized according to one or more embodiments of the present disclosure. For instance, a computing device 658 can have a number of components coupled thereto.

The computing device 658 can include a processor 660 and a memory 662. The memory 662 can have various types of information including data 664 and executable instructions 666, as discussed herein.

The processor 660 can execute instructions 666 that are stored on an internal or external non-transitory computer device readable medium (CRM). A non-transitory CRM, as used herein, can include volatile and/or non-volatile memory.

Volatile memory can include memory that depends upon power to store information, such as various types of dynamic random access memory (DRAM), among others. Non-volatile memory can include memory that does not depend upon power to store information.

Memory 662 and/or the processor 660 may be located on the computing device 658 or off of the computing device 658, in some embodiments. As such, as illustrated in the embodiment of FIG. 6, the computing device 658 can include a network interface 668. Such an interface 668 can allow for processing on another networked computing device, can be used to obtain information about the patient, and/or can be used to obtain data and/or executable instructions for use with various embodiments provided herein.

As illustrated in the embodiment of FIG. 6, the computing device 658 can include one or more input and/or output interfaces 670. Such interfaces 670 can be used to connect the computing device 658 with one or more input and/or output devices 672, 674, 676, 678, 680.

For example, in the embodiment illustrated in FIG. 6, the input and/or output devices can include a scanning device 672, a camera dock 674, an input device 676 (e.g., a mouse, a keyboard, etc.), a display device 678 (e.g., a screen showing a user interface), a printer 680, and/or one or more other input devices. The input/output interfaces 670 can receive executable instructions and/or data, storable in the data storage device (e.g., memory), representing photographs and/or video of teeth of a user.

In some embodiments, computing device 658 can be a mobile device (e.g., mobile device 218, 318, 418, 518, previously described in connection with FIGS. 1-5). The processor 660 can execute instructions 666 to perform a method, including determining whether a mobile device holder (e.g., mobile device holder 208, 330, 444, 554, previously described in connection with FIGS. 2-5, respectively) has positioned the mobile device in a correct orientation with respect to a user's teeth based on an input received by camera 674 of the mobile device. For example, camera 674 can determine whether the mobile device is at the correct length and/or angle with respect to the user's teeth to take an image (e.g., photograph and/or video) of the user's teeth. A cheek of the user can be held away from the mouth of the user to expose the teeth of the user via a cheek retractor (e.g., cheek retractor 100, 200, previously described in connection with FIGS. 1 and 2, respectively) that includes one or more imaging markers (e.g., imaging markers 104, 204, previously described in connection with FIGS. 1 and 2, respectively). The photograph and/or video of the user's teeth include one or more of the imaging markers.

The processor 660 can execute instructions 666 to generate instructions to capture photographs and/or video of teeth of a user. The instructions to capture photographs and/or video of teeth of the user can include preparation instructions with respect to setting up a mobile device holder, such as a mobile device holder 208, 330, 444, and/or 554, previously described in connection with FIGS. 2-5, respectively. The preparation instructions of the mobile device holder can ensure photographs and/or video of the teeth of the user are consistent as dental treatment progresses. The preparation instructions can be carried out by the user and/or a treatment professional.

In some examples, the processor 660 can execute instructions 666 to generate preparation instructions including instructions to attach a mobile device holder (e.g., mobile device holder 208, previously described in connection with FIG. 2) to a cheek retractor (e.g., cheek retractor 100, 200, previously described in connection with FIGS. 1A, 1B, and FIG. 2). In some examples, the processor 660 can execute instructions 666 to generate preparation instructions including instructions to assemble a mobile device holder (e.g., mobile device holder 330, 444, and/or 554, previously described in connection with FIGS. 2-5, respectively), set a table guide on a flat surface in front of the user, and set the assembled mobile device holder on the table guide.

In some examples, the processor 600 can execute instructions 666 to generate preparation instructions including instructions to place the mobile device on the mobile device holder. For example, the instructions can include instructions to place the mobile device on the mobile device holder attached to the cheek retractor or the assembled mobile device holder placed on the flat surface in front of the user.

In some examples, the processor 600 can execute instructions 666 to generate preparation instructions including calibration instructions for the mobile device. For example, the calibration instructions for the mobile device may include generating instructions to move the mobile device holder closer to the user or farther away from the user, and/or to move the mobile device holder to various angles relative to the teeth of the user. In response to the mobile device holder being in a correct position, the processor 600 can execute instructions 666 to generate an indicator that the mobile device holder is in a correct position and generate instructions to mark a position of the mobile device holder at the correct position, including marking a position on the mobile device holder and/or on the table guide. The instructions to move the mobile device can be repeated for different positions and angles such that various correct positions can be marked on the mobile device holder and/or the table guide.

In some examples, the calibration instructions may include instructions to modify flash settings of the mobile device. As used herein, the term "flash settings" can refer to photographic flash, where photographic flash refers to a flash of artificial light to help illuminate a scene during a photograph and/or video capture sequence of a camera (e.g., camera 674) of the mobile device. For example, the instructions to modify flash settings can include instructions to turn a flash on or off, modify an intensity of the flash, a length of the flash, among other flash settings of the mobile device. The flash settings can be modified based on an illumination level of a scene (e.g., illumination of a user's teeth).

In some examples, the processor 600 can execute instructions 666 to generate photograph and/or video capture instructions. The photograph and/or video capture instructions can include instructions to change a position of the mobile device, instructions to take a photograph and/or video f teeth of a user, instructions to take at least one of a number of photographs and video of the user's teeth at a number of different positions, among other photograph and/or video capture instructions, as is further described herein.

The processor 660 can execute instructions 666 to generate an instruction for the mobile device holder to change the position of the mobile device in response to the input indicating the mobile device is in an incorrect position or orientation. For example, if a mobile device is too far away and/or at a wrong angle with respect to a user's teeth, the mobile device is in an incorrect orientation. The mobile device can generate an instruction, including an audio and/or visual instruction to the user, to change the position of the mobile device. The visual instruction can be displayed on display 678 of the mobile device that includes a user interface.

Generating an instruction for the mobile device holder to change the position of the mobile device can include generating an instruction for the mobile device holder to change a distance from the mobile device to the teeth of the user. For example, if the mobile device is too close to teeth of the user, the mobile device can generate an instruction to inform the user to move the mobile device further away from the teeth. This can be accomplished, for example, by sliding the base (e.g., base 216) of the mobile device holder away from the teeth of the user, as described in connection with FIG. 2, or by moving the stand (e.g., stand 332, 432, 532) of the mobile device holder away from the teeth of the user, as described in connection with FIGS. 3-5. The correct position can correspond to the marked position on the mobile device holder and/or the table guide, as described above.

Generating an instruction for the mobile device holder to change the position of the mobile device can include generating an instruction for the mobile device holder to change an angle of the mobile device with respect to the teeth of the user. For example, if the mobile device is at an incorrect angle with respect to the teeth of the user, the mobile device can generate an instruction to inform the user to change the angle of the mobile device relative to the teeth. This can be accomplished, for example, by swiveling the arm (e.g., arm 210) of the mobile device holder about an adjustment mechanism (e.g., adjustment mechanism 212), as described in connection with FIG. 2, or by moving the stand (e.g., stand 332, 432, 532) to a different angle with respect to the teeth of the user, as described in connection with FIGS. 3-5. The correct position can correspond to the marked position on the mobile device holder and/or the table guide, as described above.

The processor 660 can execute instructions 666 to generate an instruction to take at least one of a photograph and video of the user's teeth in response to the input indicating the mobile device is in a correct orientation. For example, if the mobile device is in the correct orientation for an image of the user's teeth, the mobile device can generate an instruction, including an audio and/or visual instruction to the user, take a photograph and/or a video of the user's teeth.

The processor 660 can execute instructions 666 to generate an instruction to take at least one of a number of photographs and video of the user's teeth at a number of different positions. For example, an instruction can be generated to take eight total photographs of the user's teeth at four different positions, resulting in the user taking two photos at each position (e.g., a specified distance and angle from the teeth of the user). The different positions can correspond to the marked correct positions on the mobile device holder and/or the table guide, as described above.

The processor 660 can execute instructions 666 to generate an instruction to repeat the method until a threshold number of photographs or video are taken at the number of different positions. Continuing with the above example, the threshold number of photographs can be eight photographs. The instruction to take a photograph at the number of different positions can be repeated until the threshold number of photographs at the number of different positions is reached. The threshold number of photographs or video and the number of different positions can be configurable and/or predetermined. For example, the threshold number of photographs can be more or less than eight photographs, and the threshold number of positions can be more or less than four different positions.

In some embodiments, computing device 658 can be a server or other computing device. The processor 660 can execute instructions 666 to receive at least one of photographs and video of teeth of a user. For example, computing device 658 can receive the photographs of the user's teeth as described above (e.g., from a mobile device). Each of the at least one of the photographs and video include imaging markers, where each imaging marker is located a predefined distance from the remaining imaging markers, and where the imaging markers are included on a cheek retractor (e.g., cheek retractor 100, 200, previously described in connection with FIGS. 1 and 2, respectively), configured to hold a cheek away from a mouth of the user to expose the teeth of the user.

The processor 660 can execute instructions 666 to determine a scale for the teeth of the user based on an analysis of at least one of a size of a particular imaging marker or the distance between at least two of the imaging markers included in the at least one of the photographs and video of the teeth of the user. The distance between the imaging markers can be predefined based on the cheek retractor.

Determining the scale for the teeth can include equating the predefined distances between at least two of the imaging markers included in the at least one of the photographs to pixels in the photographs and/or video of the teeth. For example, computing device 658 can utilize the predefined distance between at least two of the imaging markers (e.g., 2.3 cm) to determine the number of pixels between the same imaging markers (e.g., 10 pixels). Based on the analysis, the computing device 658 can determine a number of pixels per cm. Computing device 658 can then determine dimensions of the user's teeth using the scale (e.g., pixels per cm).

The processor 660 can execute instructions 666 to combine photographs of the teeth of the user using the imaging markers as a reference point for consecutive images of the photographs and/or video of the teeth. For example, a user may have an image of the teeth of the user at an angle and an image of the teeth of the user from in front of the user. Computing device 658 can combine the two images using the imaging markers as a common reference point between the two consecutive images.

The processor 660 can execute instructions 666 to generate a scaled model of the teeth of the user using the determined scale for the teeth of the user. For example, the teeth can be scaled and the images of the user's teeth can be combined to generate the scaled model of the teeth. The model can be a 2D model or a 3D model.

The processor 660 can execute instructions 666 to compare the scaled model of the teeth of the user to a predefined model of teeth of the user. The models can be compared for progress tracking of a user's dental procedure. For example, a user may have had a scan of the user's dentition in a beginning stage of the dental procedure. During the procedure, the user takes images of the user's teeth and the scaled model of the teeth is created as the user's dental procedure progresses. The scaled model of the teeth as the user's dental procedure progresses can be compared against the scan of the patient's dentition in the beginning stage of the procedure used to create an ideal model of the patient's dentition during the course of treatment. The comparison can allow a treatment professional to determine whether the user's dental procedure is proceeding as expected, and/or if changes to the dental procedure need to be made.

The embodiments of the present disclosure can provide a number of benefits. For example, the cheek retractor including the imaging markers can assist in generating an accurate model of the user's teeth. The model can allow treatment professionals to determine whether the user's teeth are suitable for a particular dental procedure and/or to track an ongoing dental procedure while the user does not have to travel to the treatment professional's office. Further, utilizing mobile device holders that are consistent with the embodiments of the present disclosure can allow a user to quickly and easily take images of the user's teeth at consistent angles and distances to allow for a more accurate model of the patient's teeth to be created without the need for help from an additional person. The computing device readable medium, devices, and systems described herein can save time and improve the experience of the patient and/or treatment, among other benefits.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system for tracking a progress of an orthodontic procedure for repositioning misaligned teeth of a patient, the system comprising:
    a mobile device holder configured to provide a compressive force on a mobile device of the patient placed in the mobile device holder;
    a cheek retractor configured to attach with the mobile device holder;
    a non-transitory computing device readable medium having executable instructions that are executed by a processor to cause the mobile device to perform a method comprising:
        providing, via the mobile device, a user interface;
        instructing the patient, via video and/or audio instruction from the provided user interface, to move the mobile device holder relative to the teeth of the patient while the cheek retractor holds away a cheek of the patient to expose teeth of the patient, while taking one or more photographs and/or video of the exposed teeth using a camera of the mobile device;
        storing the one or more photographs and/or video of the teeth of the patient; and
        transmitting the one or more photographs and/or video of the teeth of the patient for tracking the progress of the orthodontic procedure of the patient by a treatment professional without the patient having to visit the treatment professional.

2. The system of claim 1, wherein performing the method further comprises determining, based on a received input from the camera of the mobile device, whether the mobile device is positioned in a correct orientation with respect to the teeth of the patient.

3. The system of claim 2, wherein performing the method further comprises generating an instruction to the patient to change a position or angle of the mobile device when the mobile device is determined to be in an incorrect orientation.

4. The system of claim 1, wherein performing the method further comprises modifying a flash setting of the camera prior to capture of the one or more photographs and/or video of the teeth.

5. The system of claim 4, wherein the flash setting of the camera is modified in response to analyzing an illumination level of the teeth.

6. The system of claim 5, wherein instructions for modifying the flash setting of the camera of the mobile device are provided based on the illumination level of the teeth.

7. The system of claim 4, wherein a length of a flash is modified prior to capture of the one or more photographs and/or video.

8. The system of claim 4, wherein an intensity of a flash is modified prior to capture of the one or more photographs and/or video.

9. The system of claim 1, wherein the user interface is configured to be presented to the patient off a reflective surface.

10. The system of claim 1, wherein the mobile device holder comprises one or more adjustable stops having a plastic material and a rubber and wherein the rubber provides friction to assist in preventing movement of the mobile device.

11. The system of claim 1, wherein the cheek retractor comprises a first lip holder and a second lip holder.

12. The system of claim 11, wherein the first lip holder and the second lip holder are coupled together by a bridge.

13. The system of claim 1, wherein a position of the mobile device relative to the cheek retractor is adjustable by adjusting the mobile device holder.

14. The system of claim 13, wherein the position of the mobile device relative to the cheek retractor is adjustable by adjusting an adjustment mechanism coupled to an arm of the mobile device holder, and wherein the arm of the mobile device holder is configured to attach to the cheek retractor.

15. The system of claim 1, wherein the cheek retractor comprises one or more imaging markers.

16. A system for tracking a progress of an orthodontic procedure for repositioning misaligned teeth of a patient, the system comprising:
a mobile device holder configured to provide a compressive force on a mobile device of the patient;
a pair of lip holders configured to attach with the mobile device holder and to fit into the patient's mouth to expose the patient's teeth;
a non-transitory computing device readable medium having executable instructions that are executed by a processor to cause the mobile device to perform a method comprising:
providing, via the mobile device, a user interface;
instructing the patient, via the provided user interface, to move the mobile device holder relative to the patient's teeth while the pair of lip holders exposes the patient's teeth, while taking one or more photographs and/or video of the exposed teeth using a camera of the mobile device, the user interface instructing the patient using video and/or audio instructions, wherein instruction the patient comprises determining, based on a received input from the camera of the mobile device, whether the mobile device is positioned in a correct orientation with respect to the patient's teeth and instructing the patient to change a position or angle of the mobile device when the mobile device is determined to be in an incorrect orientation;
storing the one or more photographs and/or video of the patient's teeth; and
transmitting the one or more photographs and/or video of the patient's teeth to a networked computing device for tracking the progress of the orthodontic procedure of the patient by a treatment professional without the patient having to visit the treatment professional.

17. A non-transitory computing device readable medium having executable instructions that are executed by a processor to cause a mobile device to perform a method of tracking a progress of an orthodontic procedure for repositioning misaligned teeth of a patient, the method comprising:
providing, via the mobile device, a user interface;
placing the mobile device in a mobile device holder configured to provide a compressive force on the mobile device and to attach the mobile device holder and a cheek retractor;
instructing the patient, with visual and/or audio instructions from the user interface, to use the cheek retractor to hold away a cheek of the patient to expose teeth of the patient while taking one or more photographs and/or video of the exposed teeth of the patient using a camera of the mobile device;
instructing the patient to change an angle of the mobile device with respect to the teeth of the patient to take the one or more photographs and/or video of the teeth of the patient from a plurality of different positions;
capturing the one or more photographs and/or video of the teeth of the patient, whereby the captured one or more photographs and/or video of the teeth of the patient is in different positions used for tracking the progress of the orthodontic procedure of the patient by a treatment professional without the patient having to visit the treatment professional.

18. The non-transitory computing device readable medium of claim 17, further comprising instructing the patient, via the user interface, to move the mobile device holder relative to the teeth of the patient while the cheek retractor holds away the cheek of the patient to take the one or more photographs and/or video of the exposed teeth of the patient.

19. The non-transitory computing device readable medium of claim 17, further comprising determining whether the mobile device is at a correct position with respect to the teeth of the patient.

20. The non-transitory computing device readable medium of claim 17, further comprising determining whether the mobile device is at a correct angle with respect to the teeth of the patient.

21. The non-transitory computing device readable medium of claim 17, wherein the method further comprises generating a model from the captured one or more photographs and/or video and comparing the model generated from the captured one or more photographs and/or video to a predefined model of the teeth of the patient to track the progress of the orthodontic procedure.

22. The non-transitory computing device readable medium of claim 17, wherein the captured one or more photographs or video of the teeth of the patient includes one or more imaging markers of the cheek retractor.

23. The non-transitory computing device readable medium of claim 17, wherein a flash setting of the camera is modified prior to capture of the one or more photographs and/or video of the teeth of the patient.

24. The non-transitory computing device readable medium of claim 23, wherein the method further comprises analyzing an illumination level of the teeth of the patient in a received input and wherein the flash setting of the camera is modified in response to analyzing the illumination level.

25. The non-transitory computing device readable medium of claim 24, wherein the method further comprises providing instructions for modifying the flash setting of the camera via the user interface.

26. The non-transitory computing device readable medium of claim 23, wherein a length of a flash is modified prior to capture of the one or more photographs and/or video.

27. The non-transitory computing device readable medium of claim 23, wherein an intensity of a flash is modified prior to capture of the one or more photographs and/or video.

28. The system of claim 1, wherein transmitting the one or more photographs and/or video of the teeth of the patient comprises transmitting to a networked computing device.

\* \* \* \* \*